US010323127B2

(12) United States Patent
Berthier et al.

(10) Patent No.: US 10,323,127 B2
(45) Date of Patent: Jun. 18, 2019

(54) POLY(ASPARTIC ACID) DERIVED CO-POLYMERS FOR A CONTROLLED RELEASE OF PERFUMING INGREDIENTS

(71) Applicant: Firmenich SA, Geneva (CH)

(72) Inventors: Damien Berthier, Geneva (CH); Daniel Benczedi, Geneva (CH); Andreas Herrmann, Geneva (CH)

(73) Assignee: Firmenich SA, Geneva (CH)

( * ) Notice: Subject to any disclaimer, the term of this patent is extended or adjusted under 35 U.S.C. 154(b) by 87 days.

(21) Appl. No.: 15/551,209

(22) PCT Filed: Feb. 11, 2016

(86) PCT No.: PCT/EP2016/052875
§ 371 (c)(1),
(2) Date: Aug. 15, 2017

(87) PCT Pub. No.: WO2016/131694
PCT Pub. Date: Aug. 25, 2016

(65) Prior Publication Data
US 2018/0016396 A1 Jan. 18, 2018

(30) Foreign Application Priority Data

Feb. 17, 2015 (EP) .................................... 15155340

(51) Int. Cl.
| | | |
|---|---|---|
| *C11D 3/50* | (2006.01) |
| *C08G 73/14* | (2006.01) |
| *C11B 9/00* | (2006.01) |
| *C11D 3/37* | (2006.01) |
| *A61Q 13/00* | (2006.01) |
| *A61Q 15/00* | (2006.01) |
| *A61K 8/88* | (2006.01) |
| *C11D 3/00* | (2006.01) |

(52) U.S. Cl.
CPC ............... *C08G 73/14* (2013.01); *A61K 8/88* (2013.01); *A61Q 13/00* (2013.01); *A61Q 15/00* (2013.01); *C11B 9/0003* (2013.01); *C11B 9/0034* (2013.01); *C11D 3/001* (2013.01); *C11D 3/3719* (2013.01); *C11D 3/50* (2013.01); *C11D 3/507* (2013.01)

(58) Field of Classification Search
CPC .......... C08G 73/14; A61K 8/88; A61Q 13/00; A61Q 15/00; C11B 9/0003; C11B 9/0034; C11D 3/001; C11D 3/3719; C11D 3/50; C11D 3/507; C11D 1/10; C11D 3/3703; C11D 3/3761
See application file for complete search history.

(56) References Cited

U.S. PATENT DOCUMENTS

| | | | |
|---|---|---|---|
| 4,137,180 A | 1/1979 | Naik et al. | |
| 5,236,615 A | 8/1993 | Trinh et al. | |
| 6,562,769 B1* | 5/2003 | Paatz ..................... | C11D 3/505 |
| | | | 510/101 |
| 2007/0111921 A1* | 5/2007 | Artiga Gonzalez ... | C11D 1/662 |
| | | | 510/446 |

FOREIGN PATENT DOCUMENTS

| | | |
|---|---|---|
| EP | 7998859 A1 | 10/1997 |
| WO | WO1997034986 A1 | 9/1997 |
| WO | WO2003049666 A2 | 6/2003 |
| WO | WO2008044178 A1 | 4/2008 |
| WO | WO2012113746 A1 | 8/2012 |

OTHER PUBLICATIONS

International Search Report and Written Opinion, application PCT/EP2016/052875 dated May 10, 2016.
Berthier et al., "Influence of the backbone structure on the release of bioactive volatiles . . . ", Bioconjugate Chem., 2010, vol. 21, pp. 2000-2012.
Herrmann, "Controlled release of volatiles under mild reaction conditions", Angew. Chem. Int. Ed., 2007, vol. 46, pp. 5836-5863.
Jana et al., "Cysteine functionalized polyaspartic acid", Langmuir, 2010, vol. 26, pp. 6503-6507.
Ullmann's Encyclopedia of Industrial Chemistry, "Laundry Detergents, 1. Introduction", 2012, vol. 20, pp. 355-392.
Ullmann's Encyclopedia of Industrial Chemistry, "Laundry Detergents, 2. Ingredients and Products", 2012, vol. 20, pp. 393-450.
Ullmann's Encyclopedia of Industrial Chemistry, "Laundry Detergents, 3. Production, Testing and Economic Aspects", 2012, vol. 20, pp. 451-485.
Ullmann's Encyclopedia of Industrial Chemistry, "Laundry Detergents, 4. Ecology and Toxicology", 2012, vol. 20, pp. 487-520.
Ullmann's Encyclopedia of Industrial Chemistry, "Laundry Detergents, 5. Washing conditions and Washing Machines", 2012, vol. 20, pp. 521-540.
Wolk et al., "One- and two-dimensional nuclear magnetic resonance characterization of poly(aspartic acid) . . . ", Macromolecules, 1994, vol. 27, pp. 7613-7620.

* cited by examiner

*Primary Examiner* — John R Hardee
(74) *Attorney, Agent, or Firm* — Winston & Strawn LLP

(57) ABSTRACT

The present invention relates to the field of perfumery. More particularly, it concerns co-polymers, derived from aspartic acid and comprising at least one α- or β-aspartic acid derivative capable of liberating an active molecule such as, for example, an α,β-unsaturated ketone or aldehyde. The present invention concerns also the use of polymers or co-polymers in perfumery as part of a perfuming or malodor counteracting composition, as well as the perfuming compositions or perfumed articles comprising the invention's compounds.

16 Claims, No Drawings

POLY(ASPARTIC ACID) DERIVED CO-POLYMERS FOR A CONTROLLED RELEASE OF PERFUMING INGREDIENTS

RELATED APPLICATIONS

This application is a national stage application under 35 U.S.C. § 371 filing of International Patent Application PCT/EP2016/052875, filed Feb. 11, 2016, which claims the benefit of European patent application n° 15155340.1 filed Feb. 17, 2015.

TECHNICAL FIELD

The present invention relates to the field of perfumery. More particularly, it concerns co-polymers derived from aspartic acid and comprising at least one α- or β-aspartic acid derivative capable of liberating an active molecule such as, for example, an α,β-unsaturated ketone or aldehyde. The present invention concerns also the use of polymers or co-polymers in perfumery as part of a perfuming or malodor counteracting composition, as well as the perfuming compositions or perfumed articles comprising the invention's compounds.

BACKGROUND

The perfume industry has a particular interest in derivatives which are capable of prolonging the effect of active ingredients over a certain period of time (such as pro-fragrances), for example in order to overcome the problems encountered when using perfuming ingredients which are too volatile or have a poor substantivity. In particular, the industry is interested by derivatives with an improved olfactive performance. Said improvement can be in time, in intensity or in the effective amount of active compound released. The improvement in intensity or amount of active compound released can also serve to reduce the perception of malodors.

The patent application WO 03/049666 describes a class of compounds capable of prolonging the effect of active ingredients. Amongst these compounds there are mentioned polymers, citing as specific examples a few styrene co-polymers. However, although the performance described in the examples for several monomeric derivatives is quite good, the performance described for the styrene co-polymers is relatively modest. There is therefore still a need to improve the release properties of polymer based ingredients capable of prolonging the effect of active ingredients. Moreover such prior art polymers are based on synthetic monomers such as alkene, malonate or acrylate, while it is known that there is a preference for more nature-friendly (easier to biodegrade) monomers or backbones.

The aim of the present invention is to provide alternative polymer based pro-fragrances, which avoid classical synthetic backbones (such as polyalkyl or polyacrilate structure) and/or provide improved deposition/performance. Such target is quite ambitious since it is known that by increasing the hydrophilicity (i.e. by using amino-acid backbones) of the polymers it strongly decreases the performance of the over pro-fragrance (see D. L. Berthier et al., in Bioconjugate Chem. 2010, vol. 21, pp. 2000-2012).

The invention's co-polymers are believed to have never previously been disclosed or suggested in the prior art, nor their particular performances in the field of perfume release.

DESCRIPTION OF THE INVENTION

We have now surprisingly discovered the existence of particular polymers or co-polymers derived from aspartic acid and comprising at least one β-oxy, β-carboxy or β-thio carbonyl moiety capable of liberating an active molecule and having superior performance.

As "active molecule" we mean here any molecule capable of bringing an odor benefit or effect into its surrounding environment, and in particular an odoriferous molecule, i.e. a perfuming ingredient, such as an α,β-unsaturated ketone or aldehyde. Said polymers or co-polymers can be used as perfuming ingredients.

Aspartic acid is known to polymerize or co-polymerize generating two different and complementary repeating units named as α- or β-form (see S. K. Wolk et al., in Macromolecules 1994, 27, 7613), of the formulae

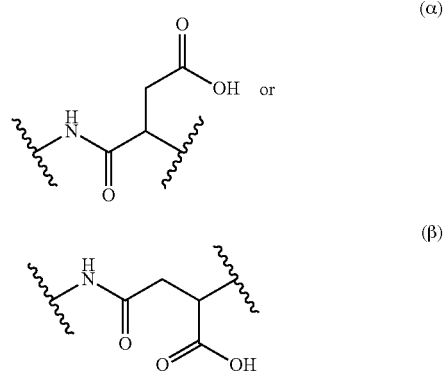

therefore also co-polymers derived from an aspartic acid comprise both forms of repeating units.

A first object of the present invention concerns a co-polymer derived from poly(aspartic acid), capable of releasing in a controlled manner an odoriferous α,β-unsaturated ketone or aldehyde, and comprising at least one repeating unit of formula (I-α) and/or (I-β)

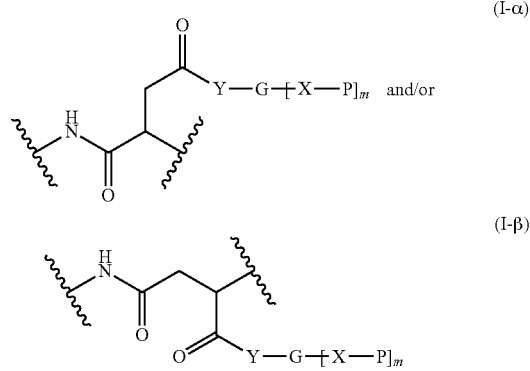

in the form of any one of their enantiomers or mixtures thereof, and wherein m is 1 or 2, and wherein the wavy lines (as for all the description) represent the bonding to another repeating unit, and P represents a radical susceptible of generating an odoriferous α,β-unsaturated ketone or aldehyde and is represented by formula (II)

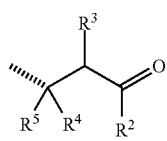

in which the hatched line indicates the location of the bond between said P and X;

R² represents a hydrogen atom, a $C_1$ to $C_{15}$ linear, cyclic or branched alkyl, alkenyl or alkadienyl radical, optionally substituted by one to four $C_1$ to $C_4$ alkyl groups; and R³, R⁴ and R⁵ represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups R¹ to R⁴ are bound together to form a saturated or unsaturated ring having 5 to 20 carbon atoms and, including the carbon atom to which said R², R³, R⁴ or R⁵ groups are bound, this ring being possibly substituted by $C_1$ to $C_8$ linear, branched or cyclic alkyl or alkenyl groups; and with the proviso that at least one of the P groups is of the formula (II) as defined hereinabove;

X represents a functional group selected from the group consisting of the formulae i) to iii):

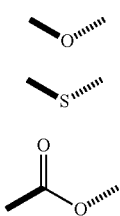

i)

ii)

iii)

in which formulae the hatched lines are as defined above and the bold lines indicate the location of the bond between said X and G;

G represents a $C_2$-$C_8$ hydrocarbon group optionally comprising 1 or 2 oxygen, sulfur and/or nitrogen atoms;

Y represents an oxygen atom, a sulfur atom or a NR⁶ group, R⁶ representing a hydrogen atom or a $C_1$-$C_4$ alkyl group.

For the sake of clarity, it is understood that when m is 2, it means that the G group is bearing two X—P units, each directly linked to said G group.

As "odoriferous α,β-unsaturated ketone or aldehyde", expression used in the definition of P, we mean here an α,β-unsaturated ketone or aldehyde which is recognized by a person skilled in the art as being used in perfumery as perfuming ingredient. By "perfuming ingredient" it is meant here a compound, which is used in a perfuming preparation or a composition to impart a hedonic effect. In other words such perfuming ingredient, to be considered as being a perfuming one, must be recognized by a person skilled in the art as being able to impart or modify in a positive or pleasant way the odor of a composition, and not just as having an odor.

In general, said odoriferous α,β-unsaturated ketone or aldehyde is a compound having from 8 to 20 carbon atoms, or even more, preferably between 10 and 15 carbon atoms.

According to any embodiment of the invention, P may represent a radical of the formulae (P-1) to (P-12), in the form of any one of its isomers:

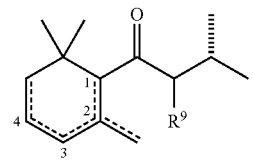
(P-1)

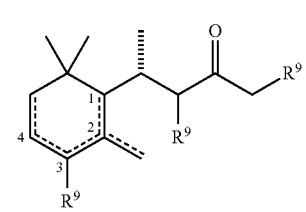
(P-2)

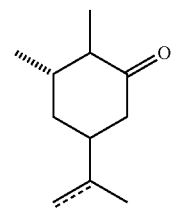
(P-3)

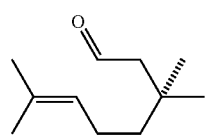
(P-4)

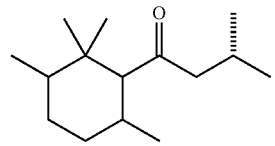
(P-5)

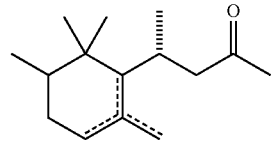
(P-6)

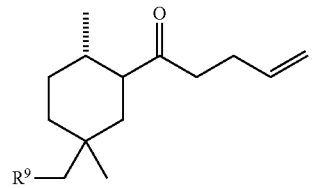
(P-7)

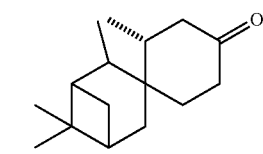
(P-8)

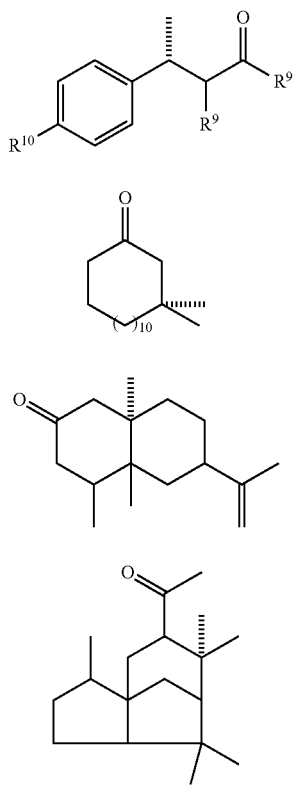

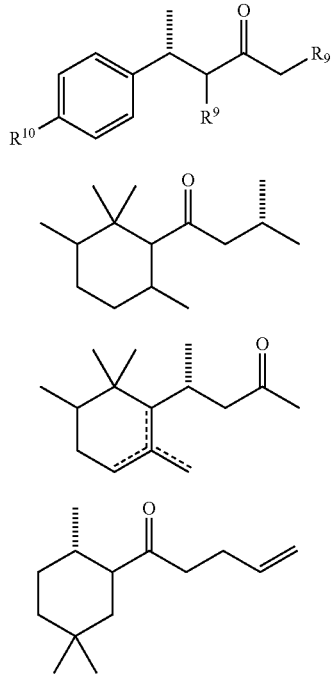

in which formulae the hatched lines have the meaning indicated above and the dotted lines represent a single or double bond, $R^9$ being a hydrogen atom or a methyl group and $R^{10}$ representing a hydrogen atom, a hydroxy or methoxy group or a $C_1$-$C_4$ linear or branched alkyl group.

According to any embodiment of the invention, P may represent a radical of the formula

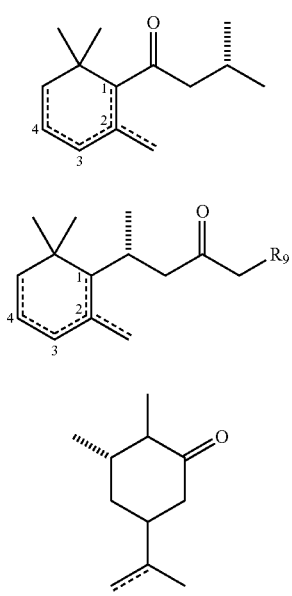

wherein hatched lines, $R^9$ and $R^{10}$ have the meaning indicated above.

According to any embodiment of the invention, P may represent a radical of the formula (P-1), (P-2), (P-3) or (P-7) as defined above. Even more particularly P may represent a compound of formula (P-1) or (P-3).

According to any embodiment of the invention, the invention's co-polymers may contain more than one repeating unit of formula (I-α) and/or (I-β), and therefore more than one group P. It is understood that when more than one group P is present the invention covers the co-polymers wherein all P have the same meaning, and/or the co-polymers wherein each P group, independently from each other, may have different meaning amongst the one defined, and in particular amongst (P-1) to (P-12).

According to any embodiment of the invention, said X represents a functional group of formula ii).

According to any embodiment of the invention, said Y represents an oxygen atom or a NR$^6$ group, R$^6$ representing a hydrogen atom or a methyl group.

According to any embodiment of the invention, said m is 1.

For the sake of clarity, by the expression "hydrocarbon group optionally comprising 1 or 2 oxygen, sulfur and/or nitrogen atoms" or the similar, it is here meant that said group, in addition to the carbon and hydrogen atom (hydrocarbon), may comprise heteroatoms and that said hereoatoms are part of a functional group, such as e.g. amines, alcohols, ethers, thioethers, esters, amides and ketones, provided said heteroatom is not directly linked to the Y or to the X group.

According to any embodiment of the invention, G may represent a $C_2$-$C_8$ hydrocarbon group optionally comprising 1 or 2 functional groups selected amongst ether, alcohol, amine, carboxylate or ester. According to any embodiment of the invention, G may represent a $C_2$-$C_5$ alkanediyl group, such as $C_2$, $C_3$ or $C_4$ linear or branched alkanediyl groups, optionally comprising one functional group selected amongst ether, carboxylate or ester.

According to any one of the above embodiments of the invention, specific examples of the moieties [P—X]$_m$-G-Y— can be the following ones:

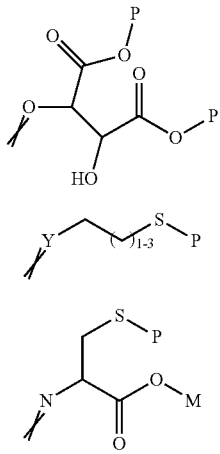

(M1)

(M2)

(M3)

wherein P and Y are as defined above, M represents a hydrogen or a an alkali metal atom or a $C_{1-6}$ alkyl chain and the crossed lines represent the single bond between the Y group and the C=O group.

According to any one of the above embodiments of the invention, the invention's co-polymers comprise at least one other repeating unit and may be optionally cross-linked.

Said other repeating units can be of the formulae (α) or (β), as defined above, as well as of the formula (χ).

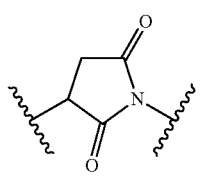

(χ)

It is self-evident that, like the repeating unit (I), also the other repeating units can be in the form of the α- and/or β-form, and for the sake of conciseness we define here an average formula (III) which is meant to represent one or the two of the (IIIα) and/or (IIIβ) forms

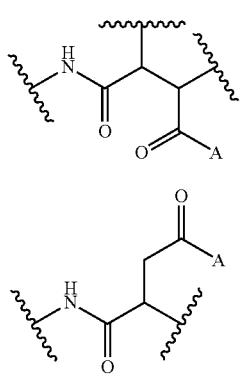

(III)

(IIIα)

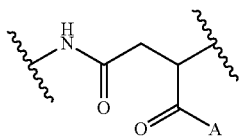

(IIIβ)

in the form of any one of their enantiomers or mixtures thereof, and wherein A may represent various groups.

According to any one of the above embodiments of the invention, the invention's co-polymers comprise at least one other repeating unit selected from the groups of the formula (III) wherein A represents:

i) a group of formula Y-G-[-X-M]$_m$, wherein m, Y, G and X are as defined above for the formulae (I-α) or (I-β), and M represents a hydrogen or a an alkali metal atom or a $C_{1-6}$ alkyl chain (in such a case the compound is also referred to as being of formula (III-i));

ii) a group of formula Y—$Z^1$, wherein Y is as defined above for the formulae (I-α) or (I-β) and preferably a $NR^6$ group, and $Z^1$ represents a $C_{1-18}$ alkyl group (in such a case the compound is also referred to as being of formula (III-ii));

iii) a group of formula Y—$Z^2$, wherein Y is as defined above for the formulae (I-α) or (I-β) and preferably a $NR^6$ group, and $Z^2$ represents a poly(oxyalkylene) chain having from 10 to 50 oxyalkylene units consisting of ethylene glycol and/or propylene glycol repeating units (i.e. Jeffamine® polyetheramines M-600, M-1000, M-2005 or M-2070, origin: Huntsman) (in such a case the compound is also referred to as being of formula (III-iii)); and/or iv) a group of formula Y—$Z^3$, wherein Y is as defined above for the formulae (I-α) or (I-β) and preferably a $NR^6$ group, and $Z^3$ represents a —(CHQ)$_n$-CH$_2$-(ortho-$C_6H_3(OH)_2$) group where n is 0 or 1, Q is a hydrogen atom or a COOM group (in such a case the compound is also referred to as being of formula (III-iv));

v) a group of formula Y—$Z^4$, wherein Y is as defined above for the formulae (I-α) or (I-β) and preferably a $NR^6$ group, and $Z^3$ represents a —(CH$_2$)$_n$—(CH$_2$)$_2$—$R^7$ group where n is 0 or 1 and $R^7$ is hydroxyl group or $N(R^8)_2$ or $N(R^8)_3Q$ groups where $R^8$ is an hydrogen atom or a $C_1$-$C_{18}$ alkyl group and Q is chloride, bromide, methylsulfonate or methylsulfate group.

The examples of specific moieties —Y-G-[-X—P]$_m$ provided above for (I) can also be applied to the units (III), provided that all P groups are replaced by M and in particular by a hydrogen atom.

According to any one of the above embodiments of the invention, the unit of formula (III-ii) are those wherein Y is a $NR^6$ group, $R^6$ being defined as above, and $Z^1$ represents a $C_{8-14}$ alkyl group, preferably linear or branched alkyl group.

According to any one of the above embodiments of the invention, the units of formula (III-iii) are those wherein Y is a $NR^6$ group, $R^6$ being defined as above, and $Z^2$ represents a poly(oxyalkylene) chain having from 30 to 50 oxyalkylene units consisting of ethylene glycol and/or propylene glycol repeating units with a ratio ethylene/propylene glycol above 1 (i.e. Jeffamine® M-2070).

According to any one of the above embodiments of the invention, the units of formula (III-iii) are those wherein Y is a $NR^6$ group, $R^6$ being defined as above, and $Z^3$ represents a 3,4-dihydroxyphenethyl group (i.e. derived from dopamine).

The invention's co-polymers can thus, amongst the total amount of all the repeating units present in the co-polymers (Tot), comprise one or several repeating units derived from aspartic acid and bearing a pro-perfume moiety P (i.e. $[(I-\alpha)+(I-\beta)]=(I)_{tot}$), and more generally one or several repeating units derived from aspartic acid (e.g. $[(I-\alpha)+(I-\beta)+(\alpha)+(\beta)+(\chi)+(III-i)+(III-ii)+(III-iii)+(III-iv)]=(Asp)_{tot}$). Said co-polymers may also comprise one or several repeating units derived from other monomeric moieties, such as other amino acids (i.e. $(Other)_{tot}$). The total amount of all the repeating units present in the co-polymers (Tot) is thus $(Tot)=(Asp)_{tot}+(Other)_{tot}$.

According to any one of the above embodiments of the invention, the invention's co-polymers can be characterized by a molar ratio $(I)_{tot}/(Tot)$ comprised between 5/100 or 40/100 and 100/100, and in particular between 70/100 and 95/100, or even between 80/100 and 90/100 or alternatively even between 5/100 and 40/100.

According to any one of the above embodiments of the invention, the invention's co-polymers can be characterized by a molar ratio $(I)_{tot}/(Asp)_{tot}$ comprised between 5/100 or 40/100 and 100/100, and in particular between 50/100 and 99/100, or even between 70/100 and 95/100 or alternatively even between 5/100 and 40/100.

According to any one of the above embodiments of the invention, the invention's co-polymers can be characterized by a molar ratio [(III-ii)]/(Tot) comprised between 0/100 and 20/100, and in particular between 5/100 and 15/100.

According to any one of the above embodiments of the invention, the invention's co-polymers can be characterized by a molar ratio [(III-iii)]/(Tot) comprised between 0/100 and 20/100, and in particular between 1/100 and 15/100, or even between 5/100 and 10/100.

According to any one of the above embodiments of the invention, the invention's co-polymers can be characterized by a molar ratio (III-ii)/(III-iv) comprised between 1/1 and 1/10, and in particular between 1/2 and 1/6.

According to any one of the above embodiments of the invention, the invention's co-polymers can be characterized by a molar ratio $(Asp)_{tot}/(Tot)$ comprised between 70/100 and 100/100, and in particular between 85/100 and 100/100, or even between 90/100 and 100/100. According to any one of the above embodiments of the invention, the invention's co-polymers can be characterized by $(Asp)_{tot}=(Tot)$ According to any one of the above embodiments of the invention, the invention's co-polymer may be characterized by a molecular weight (MW) comprised in the range between 800 Da and 200,000 Da, more particularly between 1500 Da and 100,000 Da, even more particularly between 2000 Da and 60,000 Da.

According to any one of the above embodiments of the invention, the co-polymer comprises, or consists of, units of formula (I-α), (I-β), (χ), (α), (β), (III-i), (III-ii) and (III-iv), as defined above, and wherein:

$(I)_{tot}/(Tot)$ is comprised between 5 and 40 and 100, preferably between 50 and 95, more preferably between 70 and 90.

According to any one of the above embodiments of the invention, the molecular weight (MW) can be comprised between 1000 and 150,000 Da, preferably between 1500 and 15,000, more preferably between 1800 and 5000 Da The invention's co-polymers may be in the form of a random co-polymer or of a block co-polymer. According to a particular embodiment of the invention, the co-polymer is preferentially of the random, or statistic, type.

The invention's co-polymer may be synthesized from commercially available compounds by conventional methods, such as the one mentioned herein below.

According to any one of the above-mentioned embodiments, the invention co-polymer is obtainable by a process comprising the following steps A) reacting together:

a homo- or co-polymer comprising the moiety of formula

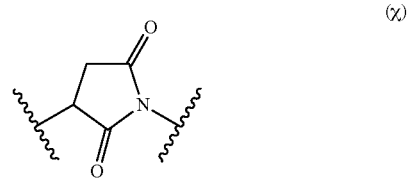 [SMILES: *C1CC(=O)N(*)C1=O]

(χ)

in the form of any one of their enantiomers or mixtures thereof; and a compound of formula $[P—X]_m$-G-Y—H, or a mixture of $[P—X]_m$-G-Y—H and at least one of the compounds $[M-X]_m$-G-Y—H, H—Y—$Z^1$, H—Y—$Z^2$ and/or H—Y—$Z^3$, wherein m, P, X, G, Y, $Z^1$, $Z^2$, $Z^3$ have the same meaning indicated above and M is a hydrogen atom when X is of formula i) or ii) or has the same meaning indicated above when X is of formula iii);

B) optionally react the co-polymer obtained in step A) with a base or an acid, for instance to at least partially hydrolyze the unreacted pyrrolidin-2,5-dione repeating unit of formula (χ).

It is understood that the ratios defined above may also apply to the starting co-polymer used in the process above described. Similarly, the same apply to the amount of $[P—X]_m$-[G-Y]$_n$—H necessary to arrive at final polymers having a ratio of $(I)_{tot}/(Tot)$ as described above, or to the amount of $(III)_{tot}$, and to any other parameter defined above.

The co-polymers used in the steps A) can be obtained according to standard methods well known from a person skilled in the art (see e.g. N. R. Jana et al., in Langmuir 2010, 26, 6503 or S. K. Wolk et al., in Macromolecules 1994, 27, 7613).

The compounds of formula $[P—X]_m$-G-Y—H are obtainable by [1,4]-addition between an odoriferous α,β-unsaturated ketone or aldehyde of formula (P')

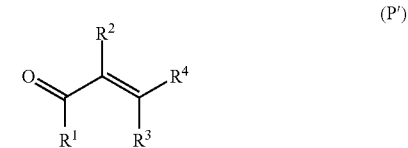

(P')

wherein the configuration of the carbon-carbon double bond can be of the (E) or (Z) type and the symbols $R^1$, $R^2$, $R^3$ and $R^4$ have the meaning indicated in formula (II); and an appropriate compound of formula $[H—X]_m$-G-Y—H, wherein all the symbols have the meanings given above. For practical reasons, in some cases (in particular when X is a group of formula i) or iii)) the invention's compounds may be more advantageously obtained by the reaction between the compound of formula (P'''), which is the aldol derivative of the odoriferous compound of formula (P'),

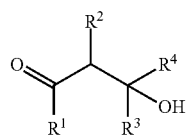
(P″)

wherein the symbols $R^1$, $R^2$, $R^3$ and $R^4$ have the meaning indicated in formula (II); and an appropriate compound (well known by a person skilled in the art) providing the moiety -G-Y—H or an equivalent thereof, such as for example a lactone if Y is an oxygen atom or a compound [H—OOC]$_m$-G-Y—H.

The use of the aldol derivative is particularly interesting for the synthesis of all the compounds of formula (I) wherein X represents, e.g., an oxygen atom or a carboxylic group. On the other hand, the direct use of the odoriferous molecule as starting material is particularly interesting for the synthesis of all the compounds of formula (I) wherein X represents a group of formula ii) or iii). These are all reactions well known by a person skilled in the art.

Step B) of the above-described process implies the hydrolysis of the unreacted repeating unit (IIIc) or the conversion of optional acidic or basic groups into the corresponding salts, e.g. -G-COOH into -G-COONa.

In general, as base can be used an alkali metal hydroxide or an earth alkali metal hydroxide. Said base can be reacted in a molar amount comprised between 1/100 and 100/100, relative to the repeating unit (Tot). Specific examples of hydroxides are NaOH or KOH. As previously mentioned, the hydrolysis can also be performed with an acid, and said acid can be any conventional acid generally used to hydrolyze a pyrrolidin-2,5-dione group. As hydrolyzing agent one can also use the medium of the consumer product to which the invention's co-polymer is added. These are all reactions well known by a person skilled in the art.

Owing to their particular chemical structure, the invention's polymers or co-polymers are capable of releasing, via a decomposition reaction, a residue and an odoriferous molecule such as, for example, an α,β-unsaturated ketone or aldehyde of formula (P').

It is not possible to provide an exhaustive list of compounds of formula (P'), which can be used in the synthesis of the compound (I) and subsequently be released. However, the following can be named as preferred examples: alpha-damascone, beta-damascone, gamma-damascone, delta-damascone, alpha-ionone, beta-ionone, gamma-ionone, delta-ionone, beta-damascenone, 3-methyl-5-propyl-2-cyclohexen-1-one, 1-(5,5- or 3,3-dimethyl-1-cyclohexen-1-yl)-4-penten-1-one, 2-methyl-5-(prop-1-en-2-yl)cyclohex-2-enone (carvone), 8- or 10-methyl-alpha-ionone, 2-octenal, 1-(2,2,3,6-tetramethyl-1-cyclohexyl)-2-buten-1-one, 4-(2,2,3,6-tetramethyl-1-cyclohexyl)-3-buten-2-one, 2-cyclopentadecen-1-one, nootkatone, cinnamic aldehyde, 2,6,6-trimethyl-bicyclo[3.1.1]heptane-3-spiro-2'-cyclohexen-4'-one and 3,7-dimethylocta-2,6-dienal (citral).

According to a particular embodiment of the invention the following compounds of formula (P') can be cited: the damascones, ionones, beta-damascenone, 1-(5,5- or 3,3-dimethyl-1-cyclohexen-1-yl)-4-penten-1-one, carvone, 1-(2,2,3,6-tetramethyl-1-cyclohexyl)-2-buten-1-one, 4-(2,2,3,6-tetramethyl-1-cyclohexyl)-3-buten-2-one and citral.

Therefore, the invention's compounds capable of releasing such compounds (P') are also a particularly appreciated embodiment of the invention.

An example of the above-mentioned decomposition reaction is illustrated in the following scheme, wherein only one repeating unit is shown:

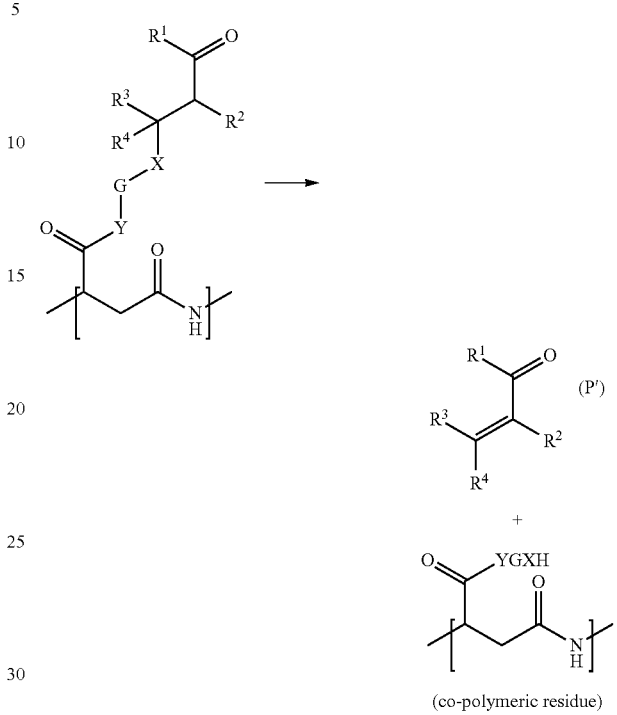

(co-polymeric residue)

The decomposition reaction, which leads to the release of the odoriferous molecules, is believed to be influenced by pH changes, by heat or by oxidation, but may also be triggered by other types of mechanisms.

As mentioned above, the invention concerns the use of the above-described co-polymers as perfuming ingredients. In other words it concerns a method to confer, enhance, improve or modify the odor properties of a perfuming composition or of a perfumed article, which method comprises adding to said composition or article an effective amount of at least a co-polymer according to the invention. By "use of an invention's co-polymer" it has to be understood here also the use of any composition containing said co-polymer and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's co-polymer as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as butylene or propylene glycols, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethanol, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castor oils such as those known under the trademark Cremophor® RH 40 (origin: BASF).

As solid carrier it is meant a material where the perfuming composition or some element of the perfuming composition can be chemically or physically bound. In general such solid carriers are employed either to stabilize the composition or to control the rate of evaporation of the compositions or of some ingredients. Solid carriers are of current use in the art, and a person skilled in the art knows how to reach the desired effect. However, by way of non-limiting examples, as solid carriers one may cite absorbing gums or polymers, such as encapsulating materials, or inorganic materials, such as porous polymers, cyclodextrins, wood based materials, organic or inorganic gels, clays, gypsum talc or zeolites.

As other non-limiting examples of solid carriers one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation techniques. As non-limiting examples one may cite in particular the core-shell encapsulation with resins of the aminoplast, polyamide, polyester, polyurea or polyurethane type or a mixture thereof (all of said resins are well known to a person skilled in the art) using techniques like phase separation process induced by polymerization, by interfacial polymerization, by coacervation or altogether (all of said techniques are have been described in the prior art), and optionally in the presence of a polymeric stabilizer or a cationic co-polymer.

Generally speaking, by "perfumery base" we mean here a composition comprising at least one perfuming co-ingredient.

Said perfuming co-ingredient is not a co-polymer according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, thiols, terpenoids, nitrogenous or sulphurous heterocyclic compounds and essential oils, and said perfuming co-ingredients can be of natural or synthetic origin or even pro-perfumes (i.e. compounds which upon degradation liberate a perfuming ingredient). Examples of pro-perfumes have been described in the literature, such as in the article published by A. Herrmann in Angewandte Chemie International Edition, 2007, vol. 46, p. 5836-5863, or in more recent work of similar type, as well as in the abundant patent literature in the field.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;

Floral ingredients: methyl dihydrojasmonate, linalool, citronellol, phenylethanol, β-(4-tert-butylphenyl)-2-methylpropanal, hexylcinnamic aldehyde, benzyl acetate, benzyl salicylate, tetrahydro-2-isobutyl-4-methyl-4 (2H)-pyranol, beta-ionone, methyl 2-(methylamino) benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydrolinalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixtures of methylionone isomers;

Fruity ingredients: gamma-undecalactone, 4-decanolide, ethyl 2-methyl-pentanoate, hexyl acetate, ethyl 2-methylbutanoate, gamma-nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethylcyclopenta-[G]isochromene, (1S,1'R)-2-[1-(3',3'-dimethyl-1'-cyclohexyl)ethoxy]-2-methylpropyl propanoate, and/or (1S,1'R)-[1-(3',3'-dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpene fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art. However, one may cite as specific non-limiting examples the following: viscosity agents (e.g. surfactants, thickeners, gelling and/or rheology modifiers), stabilizing agents (e.g. preservatives, antioxidant, heat/light stabilizer or buffers or chelating agents, such as BHT), color agents (e.g. dyes and/or pigments), preservatives (e.g. antibacterial or antimicrobial or antifungal or anti-irritant agents), abrasives, skin cooling agents, fixatives, insect repellents, ointments, vitamins and mixture thereof.

It is understood that a person skilled in the art is perfectly able to design optimal formulations for the desired effect by admixing the above mentioned components of a perfuming composition, simply by applying the standard knowledge of the art as well as by trial and error methodologies.

Other suitable perfumery adjuvants optionally used in combination with the co-polymers according to the present invention comprise tertiary amines, in particular those with high water solubility, such as triethanolamine, methyldiethanolamine, dimethylethanolamine, alkyldiethanolamines and ethoxylated alkyldiethanolamines.

According to any embodiment of the invention, a particular type of perfumery adjuvant can be selected amongst those described in WO 2012/113746, such as 5-chloro-2-methylisothiazol-3(2H)-one or 1,2-benzisothiazol-3(2H)-one, or a sulfite, such as hydrogen or sodium or potassium sulfite.

An invention's composition consisting of at least one co-polymer and at least one perfumery carrier represents a particular embodiment of the invention as well as a perfuming composition comprising at least one co-polymer, at least one perfumery carrier, at least one perfumery base, and optionally at least one perfumery adjuvant.

It is useful to mention here that the possibility to have, in the compositions mentioned above, more than one of the invention's co-polymers is important as it enables the perfumer to prepare accords, perfumes, possessing the odor tonality of various compounds of the invention, creating thus new tools for their work. The invention's polymer may also be used in the presence of other perfume delivery systems, such as capsules or pro-fragrances.

Furthermore, an invention's co-polymer, or a perfuming composition comprising it, is a useful perfuming ingredient, which can be advantageously used in all the fields of modern perfumery, such as fine perfumery or functional perfumery, to positively impart or modify the odor of a consumer product into which said compound (I) is added. Indeed, the invention's compounds may be advantageously employed in perfumery to achieve a more controlled deposition, and consequent release, of odoriferous compounds. For example, the co-polymers according to the invention, owing to a good substantivity, a low volatility and a well-controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, another object of the present invention is represented by a perfuming consumer product comprising, as a perfuming ingredient, at least one co-polymer of formula (I), as defined above.

The invention's co-polymer can be added as such or as part of an invention's perfuming composition.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises the functional formulation, as well as optionally additional benefit agents, corresponding to the desired consumer product, e.g. a detergent or an air freshener, and an olfactively effective amount of at least one invention's co-polymer. For the sake of clarity, said perfuming consumer product is a non-edible product.

The nature and type of the constituents of the perfuming consumer product do not warrant a more detailed description here, which in any case would not be exhaustive, the skilled person being able to select them on the basis of his general knowledge and according to the nature and the desired effect of said product.

Non-limiting examples of suitable perfuming consumer product can be a perfume, such as a fine perfume, a cologne or an after-shave lotion; a fabric care product, such as a liquid or solid detergent or a unidose detergent (like a powder tablet, a liquid unidose or a multichamber unidose detergent), a fabric softener, a fabric refresher, an ironing water, a paper, a bleach, a carpet cleaner, or a curtain-care product; a body-care product, such as a hair care product (e.g. a shampoo, a coloring preparation or a hair spray, a color care product or a hair shaping product), a dental care product, a disinfectant, an intimate care product), a cosmetic preparation (e.g. a skin cream or lotion, a vanishing cream or a deodorant or antiperspirant (e.g. a spray or roll on), a hair remover, a tanning, sun or after sun product, a nail product, a skin cleansing product or a makeup), a skin-care product (e.g. a perfumed soap, shower or bath mousse, oil or gel, a hygiene product or a foot/hand care product); an air care product, such as an air freshener or a "ready to use" powdered air freshener, which can be used in the home space (rooms, refrigerators, cupboards, shoes or cars) and/or in a public space (halls, hotels, malls, etc.); or a home care product, such as a mold remover, a furnisher care product, a wipe, a dish detergent or a hard-surface detergent (e.g. a floor, bath, sanitary or a windows), a leather care product; a car care product, such as a polish, waxes or a plastic cleaner.

As mentioned above, the co-polymers according to the invention, can impart a fragrance and a freshness to a treated surface, e.g. skin, which will last well beyond the rinsing and/or drying processes.

A further aspect of the present invention is a method to confer, enhance, improve or modify the odor properties of a surface, which method comprises depositing on said surface, or washing said surface with, an effective amount of at least one co-polymer according to the invention. Said surface can be any one, and one can cite as non-limiting examples, textiles, hard surfaces, hair and skin.

Some of the above-mentioned perfuming consumer product may represent an aggressive medium for the invention's co-polymer, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

Preferred perfuming compositions or perfuming consumer products are perfumes, hard surface cleaners, fabric detergents or softener bases.

Typical examples of fabric detergents or softener composition into which the co-polymer of the invention can be incorporated are described in WO 97/34986 or in U.S. Pat. Nos. 4,137,180 and 5,236,615 or EP 799 885. Other typical detergent and softening compositions which can be used are described in works such as Ullmann's Encyclopedia of Industrial Chemistry, vol. 20, Wiley-VCH, Weinheim, p. 355-540 (2012); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The above-mentioned perfuming consumer product are all characterized by being practically neutral (e.g. body care products or perfumes), acidic (e.g. fabric softeners) or basic (e.g. detergents, soaps), while the co-polymers of the invention can be either non-ionic or ionic (cationic or anionic).

We have found that, according to a particular embodiment of the invention, when the perfuming consumer product have a pH value below 6, (such as softeners) then it is preferable to combine such a base with an invention's co-polymer having an increased negative charge at basic or neutral pH as compared to acidic pH, i.e. a co-polymer comprising COOM groups.

The proportions in which the compounds according to the invention can be incorporated into the various aforementioned articles or compositions vary within a wide range of values. These values are dependent on the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 10 or even 20% by weight, or even more, of the invention's compound based on the weight of the composition into which they are incorporated. Concentrations lower than these, such as in the order of 0.001% to 5% by weight, can be used when this compound is applied directly in the perfuming of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's compound. Suitable surfaces are, in particular, textiles, hard surfaces, hair and skin.

EXAMPLES

The invention will now be described in further detail by way of the following examples, wherein the abbreviations have the usual meaning in the art, the temperatures are indicated in degrees centigrade (° C.); the NMR spectral data were recorded in dimethylsulfoxide (DMSO-$d_6$) (if not stated otherwise) on a Bruker DPX 400 spectrometer with 400 or 500 MHz for $^1$H and 100.6 or 125.8 MHz for $^{13}$C, the chemical displacements δ are indicated in ppm with respect to tetramethylsilane (TMS) as standard, coupling constants J are expressed in Hz. The distribution of monomers in co-polymers was determined by $^1$H-NMR spectroscopy.

Commercially available reagents and solvents were used without further purification, if not stated otherwise. IR Spectra: Perkin Elmer Spectrum One FTIR spectrometer, vin cm$^{-1}$.

Size exclusion chromatography (SEC) analyses were carried out at room temperature (ca. 22° C.) on a Viscotek GPC max VE 2001 GPC Solvent Sample Module connected to a Viscotek UV detector 2500, a Viscotek VE3580 RI detector and a Viscotek-270-Dual-Detector viscometer. Samples were eluted from Waters Styragel HR 4E and HP 5 (7.8×300 mm) columns at a flow rate of 1.0 mL min$^{-1}$ with tetrahydrofuran (THF, HPLC-grade). Universal calibrations were performed using commercial poly(styrene) standards. The polymer standard (ca. 40 mg) was accurately weighed and dissolved in THF (10 mL); then these solutions (100 µL) were injected for the calibration. For the molecular weights of the polymers determined by SEC, Mw stands for "weight average molecular weight" and Mn stands for "number average molecular weight". The polydispersity (PDI) is the ratio of Mw/Mn.

In the synthesis of the invention's co-polymers, by "conversion" it is meant the amount, in percentage, of the repeating unit (IIIc) converted into the repeating unit (I).

Example 1

Preparation of Polysuccinimide 1 (See N. R. Jana et al. In Langmuir 2010, 26, 6503)

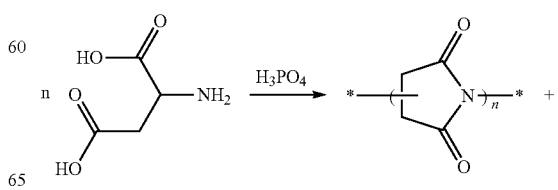

1

In a 250 mL round-bottomed flask, 2-aminosuccinic acid (100.00 g, 751 mmol) was mixed homogeneously with orthophosphoric acid (10.00 g, 751 mmol) to give a white solid. The solid was heated under vacuum at 120° C. for 1 h, then at 200° C. for 2.5 h while distilling off the water formed in the reaction. The resulting solid was crushed in a mortar, washed three times with water, the pH was adjusted to 4 with an aqueous solution of NaOH (30 wt %) and filtered twice. The solid was then dried under vacuum at 50° C. for 24 h to give a white solid (70 g, yield=96%).

$^1$H-NMR: 5.27 (m, 1H); 3.27 (m, 4.5H); 2.71 (m, 1H).
$^{13}$C-NMR: 175.46s; 173.35s; 172.27s; 47.23d; 32.46t.

Example 2 a) Preparation of Random Poly(N-Dodecyl Aspartamide-Co-Succinimide) 2

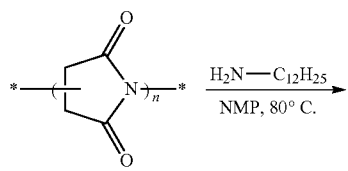

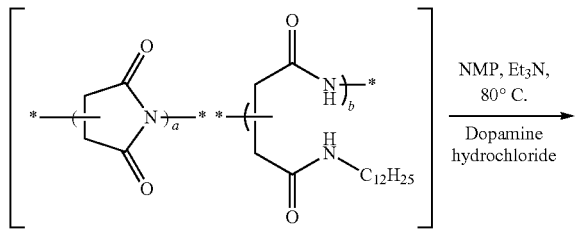

2 a = from 95/100 to 80/100, b = from 5/100 to 20/100

In a 250 mL round-bottomed flask, polysuccinimide (PSI, 1, prepared as described in Example 1, 15 g, 155 mmol of repeating units) was dissolved in N-methyl-2-pyrrolidone (NMP, 150 mL) and warmed up to 80° C. to give a solution. 1-Dodecylamine (DDA) (5 (2a), 10 (2b) or 20 mol % (2c) with respect to PSI repeating units) was added into the solution, which was heated at 80° C. for 24 h. The copolymer was precipitated and washed in diethyl ether (600 mL). The solid was dried at 50° C. under vacuum for 24 h.

General NMR Spectra:
$^1$H-NMR: 5.27; 4.57, 3.34, 3.22; 3.00, 2.68, 1.51, 1.35, 1.24, 0.86.
$^{13}$C-NMR: 173.34; 172.10; 48.46, 47.38; 32.60, 31.27, 30.08, 28.98, 28.89, 28.80, 28.68, 26.98, 25.76, 22.07, 17.19, 13.93.

b) Preparation of Random poly(succinimide-co-(N-dodecylaspartamide)-co-[N-(3,4-dihydroxy-phenethyl)aspartamide]) 3a-i

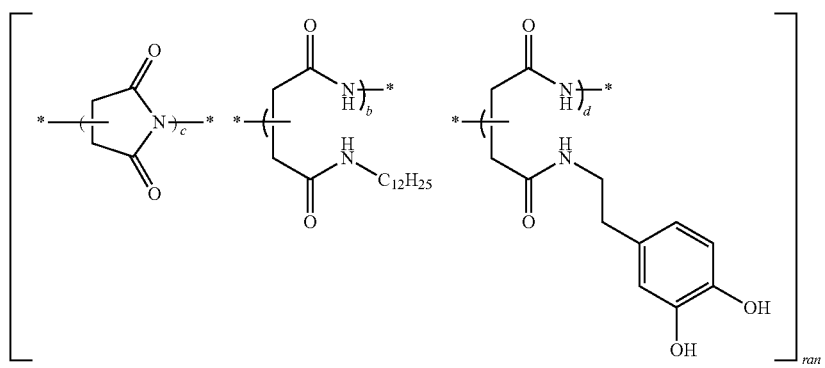

3 c = from 50/100 to 90/100, b = from 5/100 to 20/100, d = from 5/100 to 30/100

In a 100 mL round-bottomed three-necked flask, co-polymers 2a-c (5 g) were added in NMP (50 mL) and heated at 80° C. to give a yellow-orange solution. Under a flow of nitrogen, 2,3,4,6,7,8,9,10-octahydropyrimido[1,2-a]azepine (DBU, 10 mol % with respect to PSI repeating units) and triethylamine (10, 20 or 30 mol % with respect to PSI repeating units, according to the dopamine grafting density used) were added. 4-(2-Aminoethyl)benzene-1,2-diol (dopamine) hydrochloride (10 (3a-c from 2a), 20 (3d-f from 2b) or 30 mol % (3g-i from 2c) with respect to PSI repeating units) was added dropwise and the reaction mixture was stirred at 80° C. for 20 h. The reaction mixture was slowly cooled to room temperature under stirring. The co-polymer was washed with n-heptane (350 mL) to give a biphasic mixture. The lower phase was precipitated in absolute ethanol (3d-f and 3g-i) or diethyl ether (3a-c, 350 mL) and filtered to give a solid, which was dried in a drying oven at 50° C. under vacuum.

General NMR Spectra:

$^1$H-NMR: 9.85, 8.83, 8.01, 7.89, 6.68, 6.60, 6.49, 6.43, 5.26, 5.15, 5.06, 4.57, 4.54, 3.34, 3.22; 3.14, 3.00, 2.92, 2.68, 1.65, 1.62, 1.51, 1.35, 1.24, 0.86.

$^{13}$C-NMR: 174.69; 173.75; 145.30, 145.04, 144.06, 143.51, 130.22, 127.89, 119.20, 116.03, 115.90, 115.73, 115.49, 53.34, 48.46, 47.86; 45.36, 34.60, 32.39, 31.51, 31.28, 30.08, 29.01, 28.70, 28.22, 26.40, 25.91, 23.32, 22.07, 18.86, 17.20, 13.92.

| Polymers | Expected mol % | | Measured by NMR (mol %) | | Yield (%) | SEC | | |
|---|---|---|---|---|---|---|---|---|
| | (DDA) | (dopamine) | (DDA) | (dopamine) | | Mn | Mw | PDI |
| 1 | | | | | 88 | | | |
| 2a | 5 | | 4 | | 92 | | | |
| 2b | 10 | | 13 | | 99 | | | |
| 2c | 20 | | 22 | | 62 | 2800 | 5400 | 1.93 |
| 3a | 5 | 10 | 3 | 13 | 59 | | | |
| 3b | 5 | 20 | 4 | 25 | 54 | | | |
| 3c | 5 | 30 | 5 | 36 | 52 | | | |
| 3d | 10 | 10 | 8 | 9 | 49 | | | |
| 3e | 10 | 20 | 10 | 21 | 52 | | | |
| 3f | 10 | 30 | 8 | 34 | 25 | | | |
| 3g | 20 | 10 | 24 | 10 | 29 | 3200 | 19300 | 6.03 |
| 3h | 20 | 20 | 23 | 21 | 33 | 5100 | 24100 | 4.73 |
| 3i | 20 | 30 | 21 | 34 | 37 | 9000 | 55000 | 6.11 | c) Preparation of Random poly[succinimide-co-(N-dodecylaspartamide)-co-[N-(3,4-dihydroxy-phenethyl)aspartamide]-co-(N-(pyrene)methylaspartamide)] 4a-i

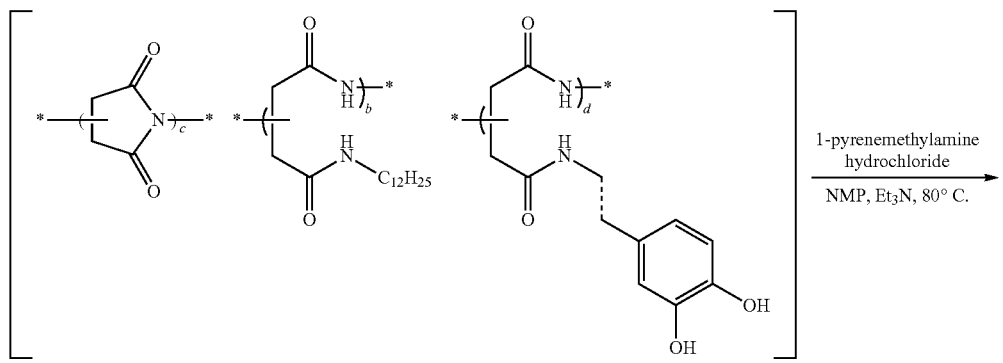

-continued

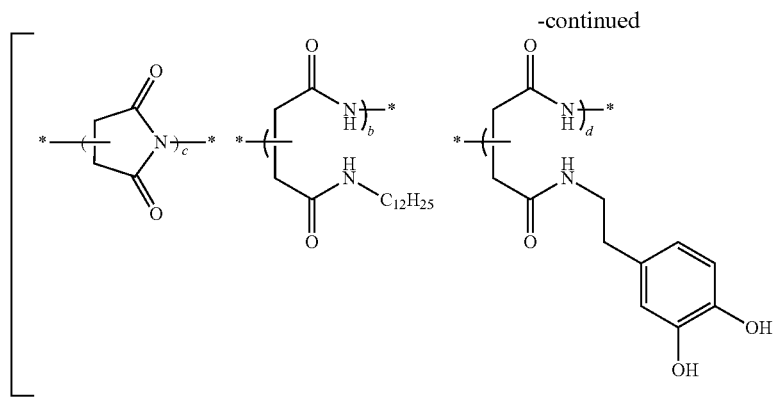 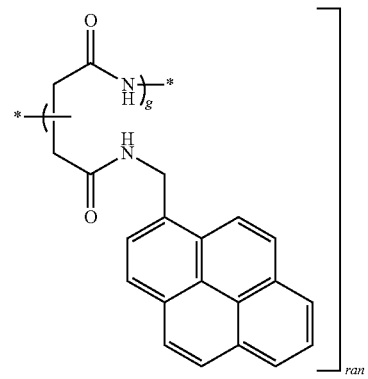

4 c = from 49.9/100 to 89.9/100, b = from 5/100 to 20/100, d = from 5/100 to 30/100, g = 0.1/100

In a 25 mL round-bottomed three-necked flask, the different co-polymers (3a-i, 0.5 g) were dissolved in NMP (5 mL) and heated at 80° C. to give an orange-brown solution. Triethylamine (0.1 mL) and 1-pyrenemethylamine hydrochloride (7.65 mg, 0.029 mmol) were dissolved in a minimum of NMP and added to the reaction mixture. The solution was heated at 80° C. for 10 h. The reaction mixture was slowly cooled to room temperature under stirring. The co-polymer was washed with n-heptane (100 mL) to give a biphasic mixture. The lower phase was precipitated in absolute ethanol or diethyl ether and filtered to give a solid, which was dried in a drying oven at 50° C. under vacuum.

General NMR Spectra:
$^1$H-NMR: 9.85; 8.83; 8.29; 8.15; 8.08; 8.01; 7.89; 6.68, 6.60, 6.49, 6.43; 5.26, 5.15, 5.06, 4.57, 4.54, 3.34, 3.22; 3.14, 3.00, 2.92, 2.68, 1.65, 1.62, 1.51, 1.35, 1.24, 0.86.

$^{13}$C-NMR: 174.69; 173.75; 145.30, 145.04, 144.06, 143.51, 130.22, 127.89, 119.20, 116.03, 115.90, 115.73, 115.49, 53.34, 48.46, 47.86; 45.36, 34.60, 32.39, 31.51, 31.28, 30.08, 29.01, 28.70, 28.22, 26.40, 25.91, 23.32, 22.07, 18.86, 17.20, 13.92.

d) Preparation of Random poly(N-(omega methyl poly(ethylene oxide-co-propylene oxide) aspartamide-co-succinimide) 5

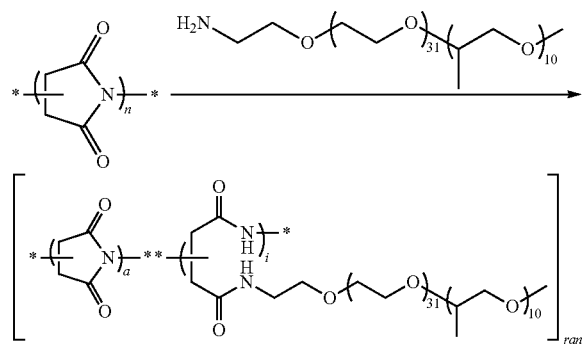

5 a = from 99/100 to 95/100, i = from 1/100 to 5/100

In a 250 mL round-bottomed flask, PSI (1, 20 g, 206 mmol of repeating units) was dissolved in N,N-dimethylformamide (DMF, 190 mL) and warmed to 90° C. to give a solution. Jeffamine® M-2070 (1 mol % (4.12 g to give 5a) or 5 mol % (20.6 g to give 5b) with respect to PSI repeating units) was added to the solution, which was heated at 90° C. for 24 h. DMF was removed and the polymer was precipitated and washed in diethyl ether (600 mL). The solid was dried at 50° C. under vacuum for 24 h.

$^1$H-NMR: 5.27; 4.57, 3.34, 3.22; 3.00, 2.68, 1.51, 1.35, 1.24, 0.86.

$^{13}$C-NMR: 173.39; 172.01; 74.13; 73.97; 71.17; 70.02; 69.92; 69.68; 67.68; 47.25; 32.48, 17.04.

e) Preparation of Random poly(N-(omega methyl poly(ethylene oxide-co-propylene oxide) aspartamide-co-succinimide) 6

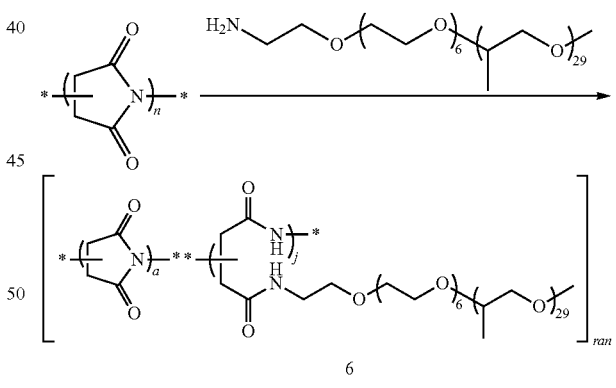

6 a = 95/100, b = 5/100

In a 250 mL round-bottomed flask, PSI (1, 10 g, 103 mmol of repeating units) was dissolved in DMF (100 mL) and warmed up to 80° C. to give a solution. Jeffamine® M-2005 (5 mol %, 10.3 g, 5.15 mmol) was added to the solution, which was heated at 80° C. for 24 h. DMF was removed and the polymer was precipitated and washed in diethyl ether (600 mL). The solid was dried at 50° C. under vacuum for 24 h.

$^1$H-NMR: 5.27, 4.52, 3.51, 3.43, 3.33, 2.69, 1.04.

$^{13}$C-NMR: 173.40, 172.20, 74.57, 72.34, 72.14, 69.69, 47.20, 32.51, 17.15.

f) Preparation of Random poly(succinimide-co-[N-(3,4-dihydroxy-phenethyl)aspartamide]) 7

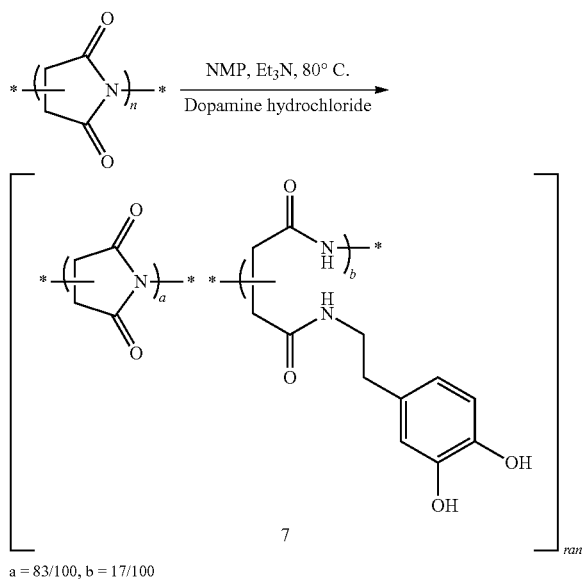

a = 83/100, b = 17/100

In a 100 mL round-bottomed three-necked flask, PSI (1, 3.4 g, 35 mmol of repeating units) was dissolved in NMP (35 mL) and warmed up to 80° C. for 2 h to give a solution. Dopamine hydrochloride (1.3 g, 20 mol % with respect to PSI repeating units) and triethylamine (1 mL) were added to the solution, which was heated at 80° C. for 20 h. After cooling to room temperature, the mixture was poured onto heptane (245 mL) and stirred for 1 h. Acetone (4.6 mL) was added to the separated NMP phase. Then the solution was added dropwise to ethanol (245 mL). The precipitate was filtered, washed with ethanol and dried at 50° C. under vacuum overnight.

$^1$H-NMR: 8.75 (br.), 7.99 (br.), 6.68, 6.67, 6.63, 6.61, 6.57, 6.49, 6.44, 6.43, 5.26 (br.), 5.20 (br.), 5.15 (br.), 4.61 (br.), 3.44, 3.30, 3.17 (br.), 3.03, 2.70 (br.), 2.50, 2.18, 1.90, 1.15, 1.06.

Example 3 a) Preparation of Random poly(succinimide-co-[N-(2-[(4-oxo-4-{2,6,6-trimethyl-cyclohex-3-en-1-yl}butan-2-yl)thio]ethyl)aspartamide]) 8

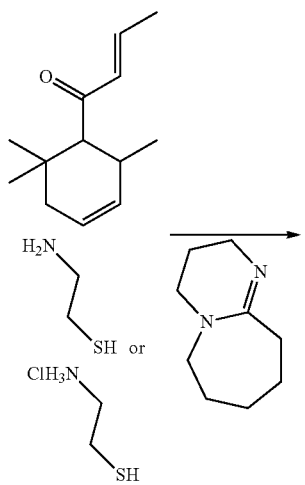

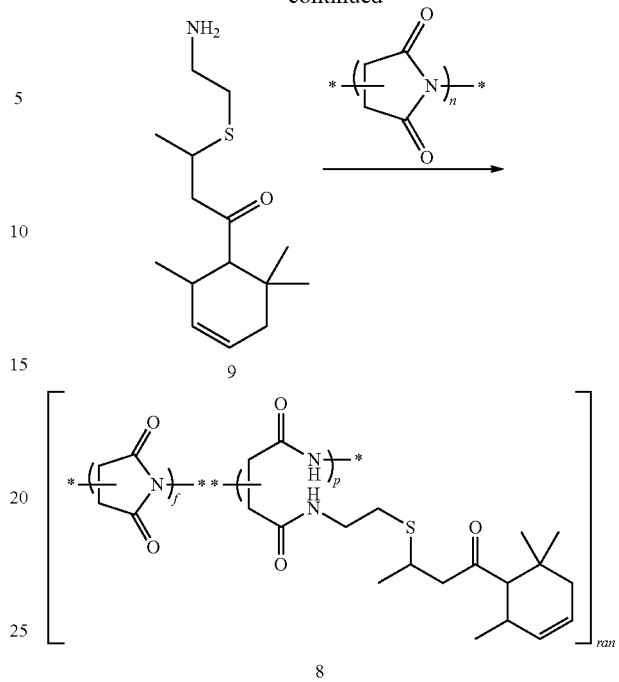

8a: f=5/100, p=95/100; 8b: f=84/100, p=16/100

9: In a 25 mL round-bottomed three-necked flask, (E)-1-((1SR,2RS)-2,6,6-trimethylcyclohex-3-enyl)but-2-en-1-one (trans-6-damascone, 1.8 g, 9.4 mmol) was dissolved in acetone (10 mL), then 2-aminoethanethiol hydrochloride (2.2 g, 18.8 mmol) and triethylamine (2.6 mL, 18.8 mmol) were added. After stirring for 5 min DBU (0.15 mL, 0.95 mmol) and more acetone (5 mL) were added. The reaction mixture was then stirred at room temperature overnight. Cyclohexane (10 mL) was added to the reaction mixture to give a precipitate which was removed by filtration. Acetone was evaporated and the reaction mixture was washed with saturated solutions of NaHCO$_3$ (20 mL) and NaCl (20 mL, 2×). The aqueous phases were re-extracted with cyclohexane (25 mL) and the organic layers dried with Na$_2$SO$_4$, filtered and concentrated to give a mixture of 3-((2-aminoethyl)thio)-1-(2,6,6-trimethylcyclohex-3-en-1-yl)butan-1-one (9, 50%) and trans-δ-damascone (13%).

8a: In a 50 mL round-bottom flask, trans-6-damascone (8.50 mL, 41.30 mmol) was added dropwise during 5 min to a suspension of 2-aminoethanethiol (3.20 g, 41.30 mmol) in NMP (5.00 mL). The reaction mixture was stirred at 0° C. for 30 min, then left warming to room temperature. DBU (0.30 mL, 2.00 mmol) was added and the reaction mixture stirred at room temperature for 2 h. Then PSI (1, 4.00 g, 41.20 mmol) in NMP (40 mL) was added. The reaction mixture was stirred at room temperature for 1 h to give an orange solution, which then was heated to 80° C. and stirred for 20 h. While stirring, the medium was slowly cooled to room temperature. Ethyl acetate (250 mL) was added and the reaction mixture was washed three times with NaCl sat. The organic layer was concentrated under reduced pressure and the polymer precipitated with n-heptane (400 mL). Filtering through a sintered glass funnel gave an orange solid (8.85 g, conversion=95%, yield=57%).

$^1$H-NMR: 5.50 (m, 1H); 5.44 (m, 1H); 5.04 (m, 0.05H); 4.52 (m, 0.95H); 3.21 (m, 3.15H); 2.84 (m, 0.85H); 2.72 (m,

2H); 2.56 (m, βH); 2.35 (m, 2H); 2.28 (m, 1H); 1.92 (m, 1H); 1.64 (m, 1H); 1.22 (m, βH); 0.94 (m, βH); 0.84 (m, 6H).

$^{13}$C-NMR: 211.70s; 171.16s; 169.32s; 131.46d; 124.12d; 61.36d; 53.24t; 40.95t; 33.70d; 32.49s; 31.09d; 29.07q; 28.89t; 21.46q; 21.27q; 20.47q; 19.37q; 19.33q; 17.12q.

IR: 3299m, 3062w, 3018w, 2957m, 2929m, 2871m, 2830w, 1783w, 1704m, 1650s, 1530s, 1455w, 1429w, 1386w, 1365m, 1297w, 1269w, 1248w, 1231w, 1192w, 1154w, 1116m, 1086m, 1040w, 999m, 933w, 895m, 842w, 747w, 688m, 638m.

8b: In a 50 mL round-bottom flask, PSI (1, 0.97 g, 10 mmol of repeating units) was dissolved in NMP (15 mL) and warmed up to 80° C. to give a solution. Then 9 (mixture, 1.1 g, 20 mol % with respect to PSI repeating units) and DBU (152 mg, 1 mmol) were added to the solution, which was heated at 80° C. for 20 h. After cooling to room temperature, the mixture was added dropwise to ether (60 mL). The precipitate (which slowly liquified) was filtered and dried at room temperature under vacuum.

b) Preparation of Random poly[succinimide-co-(N-dodecylaspartamide)-co-(N-(2-[(4-oxo-4-{2,6,6-trimethylcyclohex-3-en-1-yl}butan-2-yl)thio]ethyl) aspartamide] 10

In a 100 mL round-bottomed flask, trans-6-damascone (18.0 g, 94.0 mmol), triethylamine (13.2 mL, 95.0 mmol), and 2-aminoethanethiol hydrochloride (10.8 g, 95.0 mmol) were dissolved in acetone (30 mL) to give a colorless solution. DBU (1.4 mL, 9.5 mmol) was added. The reaction mixture was then stirred at room temperature overnight. Cyclohexane (30 mL) was added to the reaction mixture to give a precipitate which was removed by filtration. Acetone was evaporated and the reaction mixture was washed with 2M NaCl (2×50 mL), $10^{-3}$M NaOH (40 mL), and H$_2$O. The organic layer was dried with MgSO$_4$, filtered and concentrated to give 9.

Co-polymer 2b (3 g, 26 mmol) was dissolved in NMP (20 mL) at 50° C. for 1 h. Then 9 (11.2 g, 41.5 mmol) was dissolved in NMP (20 mL) and the solution was added dropwise to the solution of 2b. The reaction mixture was then stirred at 50° C. overnight. Polymer 10 was obtained after precipitation in n-heptane, filtration, and drying under vacuum for 24 h as a solid (m=5.69 g, Y=57%).

$^1$H-NMR: 8.87; 8.12, 5.52, 5.45, 5.04, 4.51, 3.56, 3.47, 3.25, 3.07, 2.93, 2.88-2.55, 2.51, 2.36, 2.31, 2.06-1.82, 1.71-1.67, 1.24, 0.96, 0.86.

$^{13}$C-NMR (CDCl$_3$): 211.85, 174.77, 168.95, 131.47, 124.09, 61.33, 54.21, 53.99, 53.26, 48.44, 47.79, 40.99, 37.42, 33.79, 33.60, 32.50, 31.38, 31.28, 31.21, 31.09, 31.04, 30.99, 30.77, 29.07, 28.97, 28.64, 28.17, 27.16, 27.08, 25.86, 26.98, 25.76, 23.27, 22.01, 21.44, 21.24, 20.61, 20.48, 19.39, 19.37, 19.33, 18.80, 17.91, 13.85.

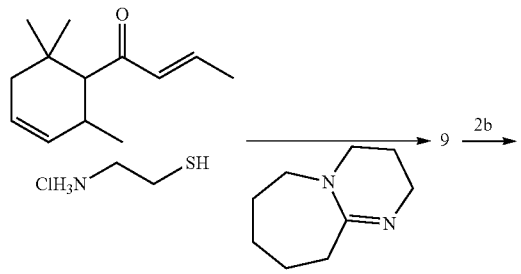

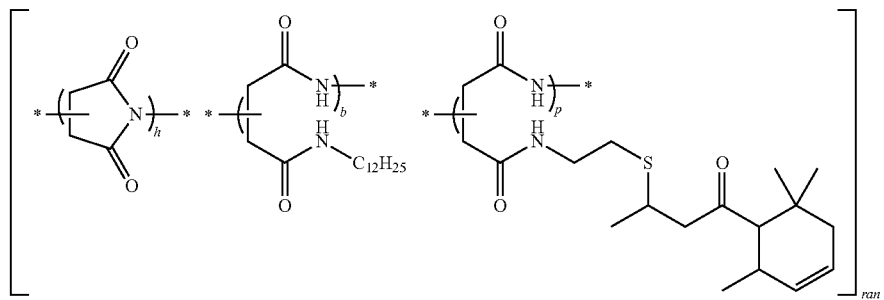

10 h = 44/100, b = 10/100, p = 46/100 c) Preparation of Random poly(succinimide-co-[N-(omega methyl poly(ethylene oxide-co-propylene oxide) aspartamide]-co-[N-(2-[(4-oxo-4-{2,6,6-trimethylcyclohex-3-en-1-yl}butan-2-yl)thio]ethyl)aspartamide]) 11

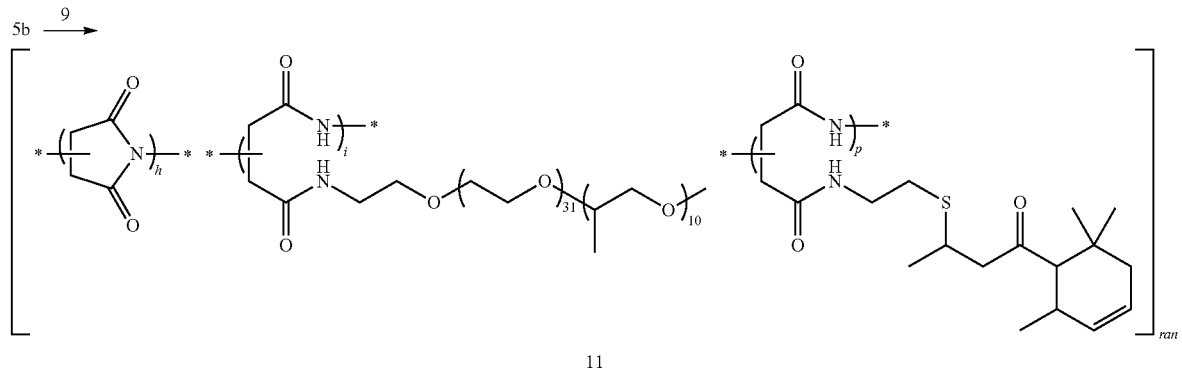

11 h = 25/100, i = 5/100, p = 70/100

Co-polymer 5b (3.0 g, 15.5 mmol) was dissolved in DMF (20 mL) at 50° C. for 1 h. Then 9 (6.7 g, 24.9 mmol) was dissolved in DMF (20 mL) and the solution was added dropwise to 5b. The reaction mixture was then stirred at 50° C. overnight. The polymer 11 was obtained after precipitation in n-heptane, filtration, and drying under vacuum for 24 h as a solid (m=1.89 g, Y=27%).

$^1$H-NMR: 8.78; 8.12, 5.52, 5.45, 4.89, 4.49, 3.55, 3.51, 3.23, 3.06, 2.90, 2.80-2.55, 2.36, 2.30, 1.98, 1.93, 1.87, 1.67, 1.63, 1.23, 1.05, 0.95, 0.86, 0.77.

$^{13}$C-NMR (CDCl$_3$): 211.86, 174.40, 171.00, 131.47, 124.14, 74.06, 69.69, 61.33, 58.20, 54.23, 54.06, 53.86, 48.03, 45.76, 40.93, 37.42, 33.79, 33.72, 33.60, 32.50, 31.09, 31.03, 29.07, 28.29, 21.44, 21.25, 20.61, 20.48, 19.37, 19.33, 17.93, 17.05.

d) Preparation of Random poly(succinimide-co-[N-(omega methyl poly(ethylene oxide-co-propylene oxide)aspartamide]-co-[N-(2-[(4-oxo-4-{2,6,6-trimethylcyclohex-3-en-1-yl}butan-2-yl)thio]ethyl)aspartamide]) 12

Co-polymer 6 (3.0 g, 15.5 mmol) was dissolved in DMF (20 mL) at 50° C. for 1 h. Then 9 (6.7 g, 24.9 mmol) was dissolved in DMF (20 mL) and the solution was added dropwise to 6. The reaction mixture was then stirred at 50° C. overnight. The polymer 12 was obtained after precipitation in n-heptane, filtration, and drying under vacuum for 24 h as a solid (m=2.51 g, Y=35%).

$^1$H-NMR: 8.70; 8.09, 5.51, 5.45, 5.04, 4.50, 3.56, 3.49, 3.33, 3.26, 3.05, 2.94, 2.80-2.55, 2.35, 2.29, 1.98, 1.93, 1.87, 1.67, 1.63, 1.22, 1.05, 0.95, 0.86, 0.77.

$^{13}$C-NMR (CDCl$_3$): 211.88, 173.98, 169.00, 131.50, 124.10, 74.48, 72.33, 72.14, 69.69, 61.33, 58.17, 54.21, 54.03, 53.28, 47.79, 45.76, 40.94, 37.48, 35.68, 34.98, 33.79, 33.60, 32.50, 31.52, 31.09, 31.04, 30.77, 30.66, 29.38, 29.06, 28.14, 27.60, 27.52, 25.83, 23.23, 21.45, 21.26, 20.61, 20.48, 19.37, 19.33, 18.77, 17.91, 17.15.

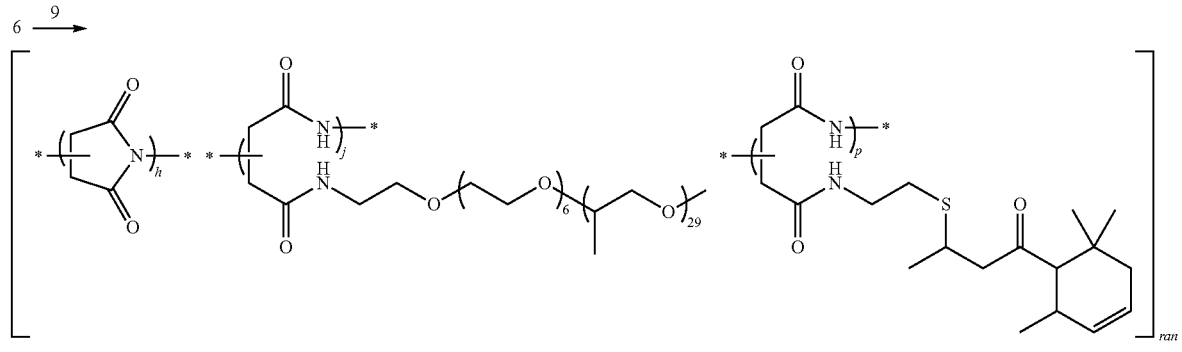

12 h = 61/100, j = 5/100, p = 34/100 e) Preparation of Random poly(succinimide-co-[N-(3,4-dihydroxyphenethyl)aspartamide]-co-[N-(2-[(4-oxo-4-{2,6,6-trimethylcyclohex-3-en-1-yl}butan-2-yl)thio]ethyl)aspartamide]) 13

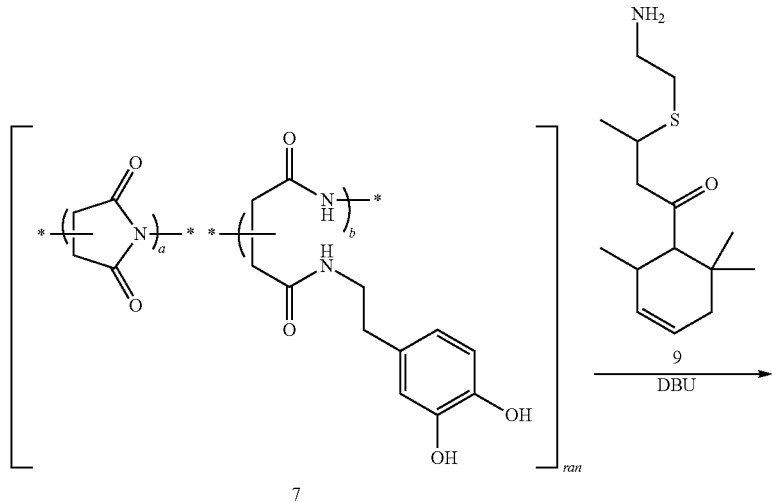

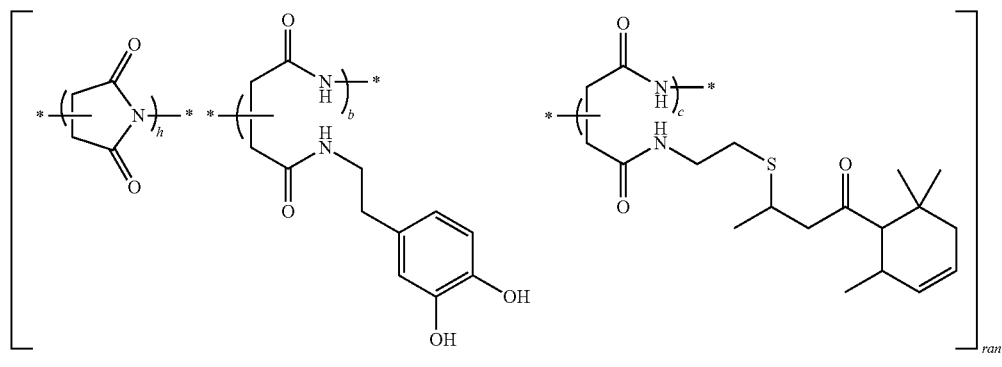

h = 68/100, b = 23/100, c = 9/100

In a 25 mL round-bottomed flask, co-polymer 7 (0.75 g, 5.1 mmol) was dissolved in NMP (7.5 mL) to give a brown solution. Then 9 (mixture prepared as described above, 0.63 g, 1.0 mmol) and DBU (77 mg, 0.5 mmol) were added. The reaction mixture was stirred at 80° C. for 20 h. After cooling to room temperature, the mixture was poured onto heptane (50 mL) and stirred for 30 min. The NMP phase was separated, added dropwise to acetone (25 mL) and stirred at room temperature for 1 h. The precipitate was filtered, washed with acetone and dried at 50° C. under vacuum overnight.

$^1$H-NMR: 9.74 (br.), 8.79 (br.), 8.13 (br.), 8.00 (br.), 7.92, 6.62, 6.61, 6.57, 6.49, 6.45, 6.43, 5.52, 5.45, 5.43, 5.26 (br.), 5.01 (br.), 4.51 (br.), 3.55, 3.54, 3.47, 3.31, 3.25, 3.15 (br.), 3.05 (br.), 2.89 (br.), 2.73 (br.), 2.70, 2.65, 2.51, 2.37, 2.30, 2.18, 2.09, 1.91, 1.66 (br.), 1.61 (br.), 1.45, 1.22 (br.), 0.95, 0.85.

f) Preparation of Random poly(succinimide-co-(N-dodecylaspartamide)-co-[N-(3,4-dihydroxyphenethyl)aspartamide]-co-[N-(2-[(4-oxo-4-{2,6,6-trimethylcyclohex-3-en-1-yl}butan-2-yl)thio]ethyl)aspartamide]) 14

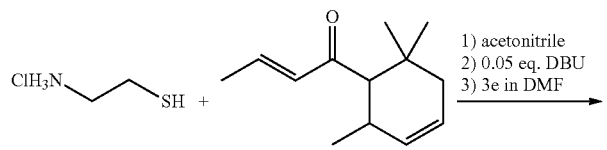

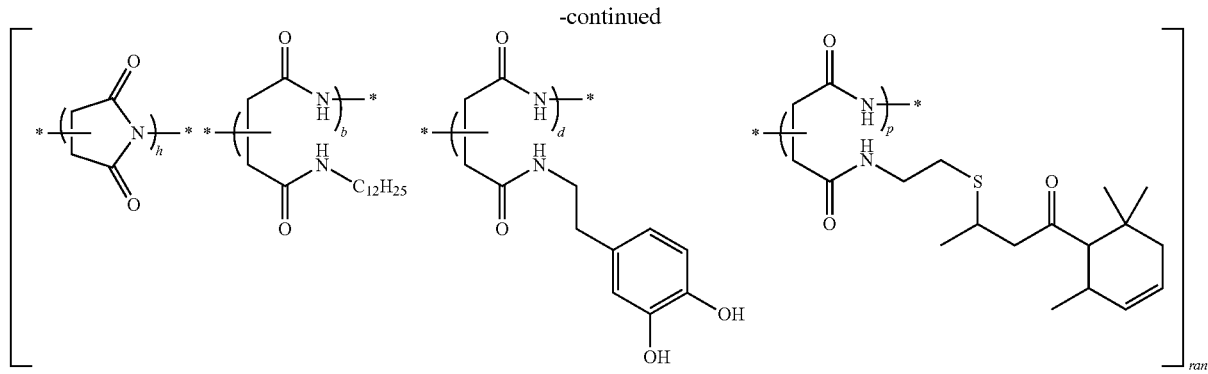

14 h = 13/100, b = 10/100, d = 21/100, p = 56/100

In a 25 mL round-bottomed flask was added trans-δ-damascone (0.58 mL, 2.81 mmol) in acetonitrile (5 mL) to give a colorless solution. 2-Aminoethanethiol hydrochloride (0.31 g, 2.76 mmol) and DBU (0.4 mL, 2.68 mmol) were added. The reaction mixture was stirred at room temperature for 3 hours. Co-polymer 3e (0.25 g, 1.68 mmol) was dissolved in DMF (5 mL) and this solution was added to the reaction mixture, which was stirred at 75° C. for 15 h. Co-polymer 14 was recovered after precipitation in heptanes and filtration (conversion=80%).

$^1$H-NMR: 9.24, 8.11, 6.63, 6.58, 6.43, 5.53, 5.45, 5.07, 4.53, 3.59, 3.48, 3.33, 3.25, 3.08, 2.95, 2.88, 2.76, 2.60, 2.36, 2.31, 1.96, 1.66, 1.26, 1.23, 0.96, 0.86.

$^{13}$C-NMR (CDCl$_3$): 211.87, 162.21, 160.99, 142.33, 134.34, 131.47, 124.14, 61.31, 54.24, 53.98, 49.48, 39.93, 37.38, 33.95, 33.63, 32.52, 31.09, 29.23, 29.06, 21.45, 21.24, 20.48, 19.41, 19.33, 15.94.

g) Preparation of Random poly(succinimide-co-(N-dodecylaspartamide)-co-[N-(3,4-dihydroxy-phenethyl)aspartamide]-co-[N-(pyrene)methylaspartamide]-co-[N-(2-(4-oxo-4-{2,6,6-trimethylcyclohex-3-en-1-yl}butan-2-yl)thiol ethyl)aspartamide]) 15

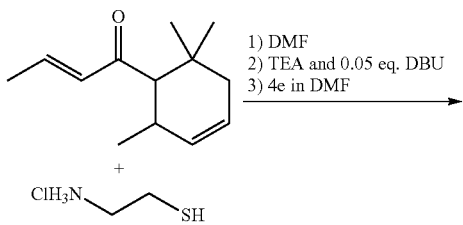

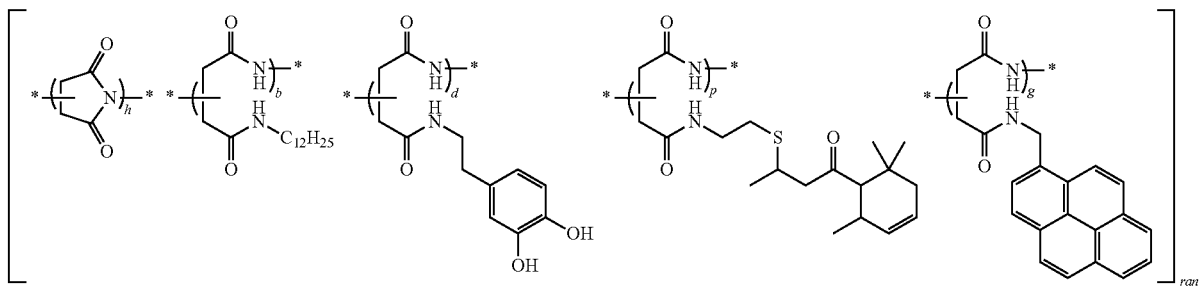

15 h = 22/100, b = 10/100, d = 21/100, p = 46/100, g = 0.1/100

In a 25 mL round-bottomed flask was added trans-6-damascone (0.24 mL, 1.16 mmol) in DMF (5 mL). 2-Aminoethanethiol hydrochloride (0.14 g, 0.74 mmol), triethylamine (0.12 mL, 1.21 mmol) and DBU (0.03 mL, 0.20 mmol) were added. The reaction mixture was stirred at room temperature for 3 hours. Co-polymer 4e (0.11 g, 0.74 mmol) was dissolved in DMF (5 mL) and this solution was added to the reaction mixture, which was stirred at 75° C. for 15 h. Co-polymer 15 was recovered after precipitation in heptanes and filtration (conversion=66%).

$^1$H-NMR: 10.03, 8.50, 6.63, 6.43, 5.53, 5.46, 5.08, 4.51, 3.55, 3.48, 3.35, 3.24, 2.90, 2.79, 2.71, 2.64, 2.36, 2.30, 1.94, 1.65, 1.24, 1.21, 0.96, 0.86.

Example 4

Preparation of Random poly(succinimide-co-[N-(2-[(4-oxo-4-{2,6,6-trimethylcyclohex-3-en-1-yl}butan-2-yl)thio]1-(methoxycarbonate)-ethyl)aspartamide]) 16

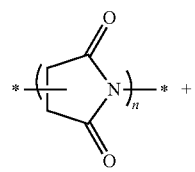

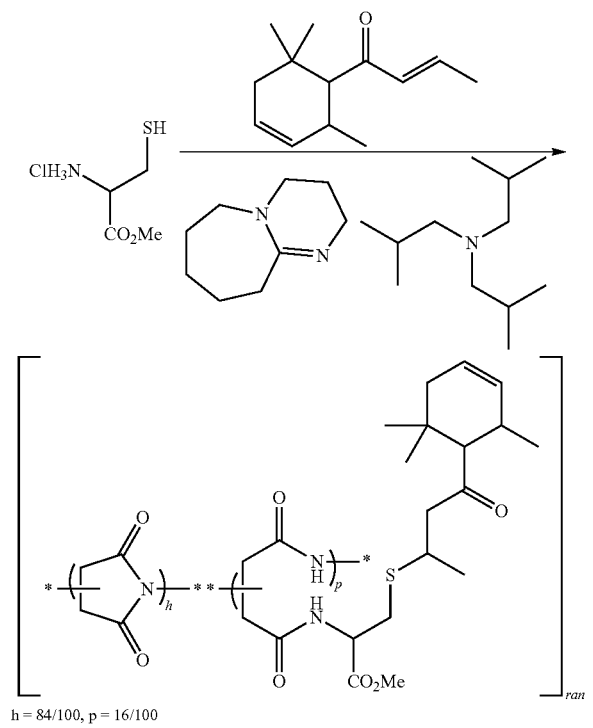

h = 84/100, p = 16/100

In a 50 mL round-bottomed flask, trans-6-damascone (3.20 mL, 15.54 mmol) was added to a suspension of 3-mercapto-1-methoxy-1-oxopropan-2-aminium chloride (2.65 g, 15.44 mmol), DBU (0.23 mL, 1.54 mmol) and triisobutylamine (7.50 mL, 31.00 mmol) in NMP (15 mL). The reaction mixture was stirred at 75° C. for 20 h. Then PSI (1, 10.50 g, 15.46 mmol) was added. The reaction mixture was stirred at 80° C. for 2 h. While stirring, the reaction mixture was slowly cooled to room temperature. The polymer was precipitated with ethyl acetate (100 mL). Filtering through sintered glass funnel and drying in a drying oven at 50° C. under vacuum gave an orange solid (1.70 g, conversion=16%, yield=82%).

$^1$H-NMR: 5.52 (m, 0.16H); 5.44 (m, 0.16H); 5.27 (m, 1H); 4.23 (m, 0.12H); 3.74 (m, 0.21H); 3.54 (m, 0.44H); 3.48 (m, 0.49H); 3.23 (m, 4.5H); 2.71 (m, 1H); 3.09 (m, 0.56H); 2.73 (m, 2H); 2.31 (m, 0.47H); 1.92 (m, 0.51H); 1.66 (m, 0.6H); 1.61 (m, 0.8H); 1.23 (m, 0.74H); 0.96 (m, 0.47H); 0.84 (m, 0.98H).

$^{13}$C-NMR: 212.60s; 173.40s; 172.60s; 131.45d; 124.15d; 61.30d; 53.30t; 52.72d; 48.46t; 47.85t; 47.74d; 47.32d; 40.87t; 37.34t; 32.61t; 31.32t; 30.08t; 28.97t; 28.24s; 25.93t; 23.35t; 20.47q; 19.31q; 18.87t; 17.19t; 13.98q.

Example 5

Preparation of Random poly(succinimide-co-[N-(2-((2-methyl-3-oxo-5-(prop-1-en-2-yl) cyclohexyl)thio)ethyl)aspartamide]) 17

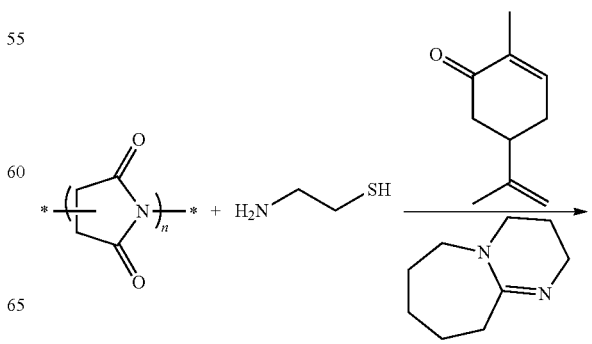

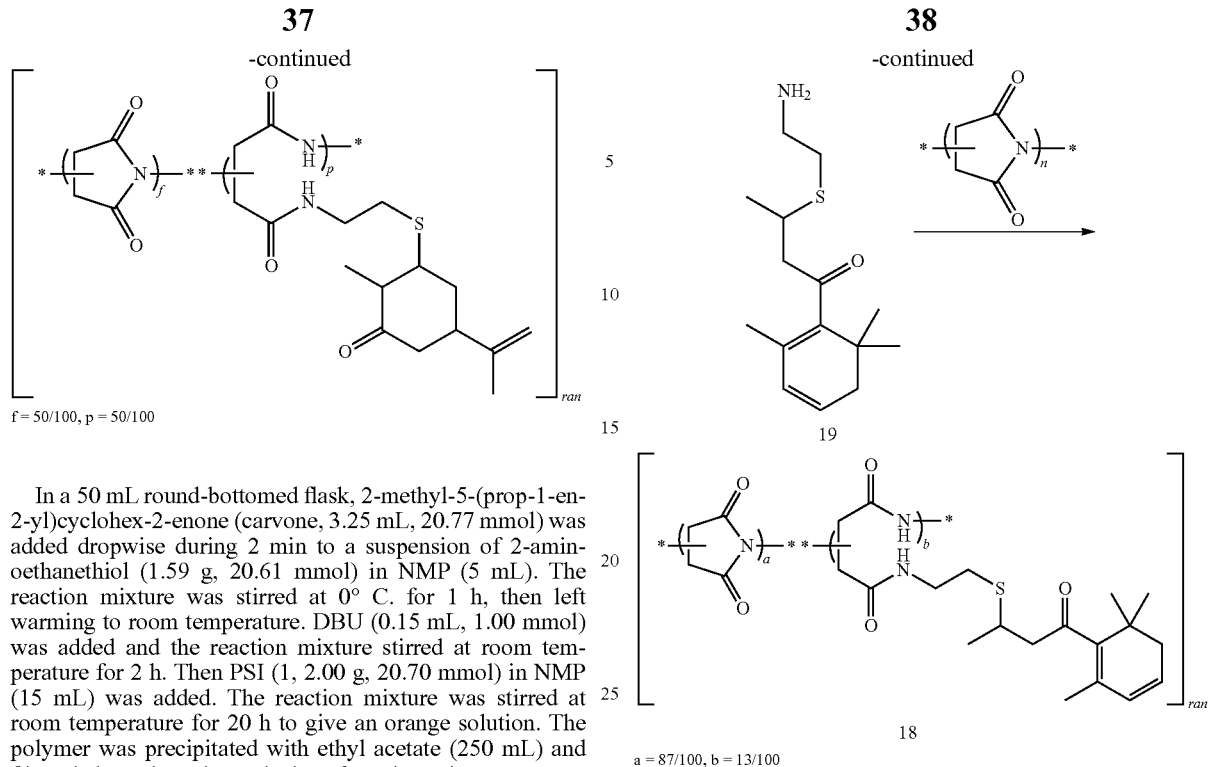

f = 50/100, p = 50/100 a = 87/100, b = 13/100

18

In a 50 mL round-bottomed flask, 2-methyl-5-(prop-1-en-2-yl)cyclohex-2-enone (carvone, 3.25 mL, 20.77 mmol) was added dropwise during 2 min to a suspension of 2-aminoethanethiol (1.59 g, 20.61 mmol) in NMP (5 mL). The reaction mixture was stirred at 0° C. for 1 h, then left warming to room temperature. DBU (0.15 mL, 1.00 mmol) was added and the reaction mixture stirred at room temperature for 2 h. Then PSI (1, 2.00 g, 20.70 mmol) in NMP (15 mL) was added. The reaction mixture was stirred at room temperature for 20 h to give an orange solution. The polymer was precipitated with ethyl acetate (250 mL) and filtered through a sintered glass funnel to give an orange solid (2.45 g, conversion=50%, yield=36%).

$^1$H-NMR: 8.08 (m, 1H); 5.05 (m, 1H); 4.68 (m, 1H); 4.50 (m, 0.7H); 3.56 (m, 0.4H); 3.47 (m, 0.8H); 3.32 (m, 0.9H); 3.25 (m, 0.7H); 3.15 (m, 2.3H); 2.97 (m, 0.8H); 2.91 (m, 0.6H); 2.81 (m, 1.4H); 2.66 (m, 0.6H); 2.63 (m, 0.6H); 2.33 (m, 1.4H); 2.05 (m, 1.3H); 1.91 (m, 0.5H); 1.72 (m, 0.8H); 1.67 (m, 1.8H); 1.61 (m, 0.8H); 1.52 (m, 0.3H); 1.34 (m, 0.4H); 1.21 (m, 0.5H); 1.12 (m, 0.4H); 1.06 (m, 0.4H); 0.95 (m, 0.3H).

$^{13}$C-NMR: 175.30s; 168.90s; 165.30s; 148.44s; 109.20t; 86.69s; 85.41s; 55.99s; 53.37t; 50.90t; 49.24d; 47.87t; 46.14t; 45.05d; 43.35d; 42.05d; 41.65d; 41.55d; 37.59t; 35.52t; 35.40t; 31.65t; 28.22t; 25.91t; 23.31t; 20.78q; 20.70q; 18.86t; 14.58q; 13.84q; 12.41q; 10.29q.

Example 6 a) Preparation of Random poly(succinimide-co-[N-(2-[(4-oxo-4-{2,6,6-trimethyl-cyclohexa-1,3-dien-1-yl}butan-2-yl)thio]ethyl)aspartamide]) 18

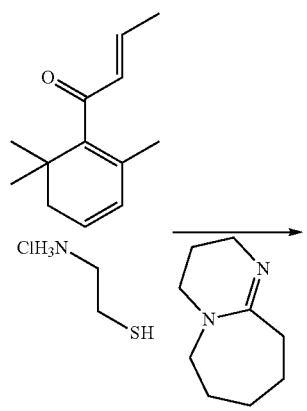

In a 25 mL round-bottomed three-necked flask, (E)-1-(2,6,6-trimethylcyclohexa-1,3-dien-1-yl)but-2-en-1-one (damascenone, 1.8 g, 9.4 mmol) was dissolved in acetone (10 mL), then 2-aminoethanethiol hydrochloride (2.2 g, 18.8 mmol) and triethylamine (2.6 mL, 18.8 mmol) were added. After stirring for 5 min DBU (0.15 mL, 0.95 mmol) and more acetone (5 mL) were added. The reaction mixture was then stirred at room temperature overnight. Cyclohexane (10 mL) was added to the reaction mixture to give a precipitate which was removed by filtration. Acetone was evaporated and the reaction mixture was washed with saturated solutions of NaHCO$_3$ (20 mL) and NaCl (20 mL, 2×). The aqueous phases were re-extracted with cyclohexane (25 mL) and the organic layers dried with Na$_2$SO$_4$, filtered and concentrated to give a mixture of 3-((2-aminoethyl)thio)-1-(2,6,6-trimethylcyclohexa-1,3-dien-1-yl)butan-1-one (19, 44%), and damascenone (28%).

In a 50 mL round-bottom flask, PSI (1, 0.97 g, 10 mmol of repeating units) was dissolved in NMP (15 mL) and warmed up to 80° C. to give a solution. Then 19 (mixture, 1.2 g, 20 mol % with respect to PSI repeating units) and DBU (0.15 mL) were added to the solution, which was heated at 80° C. for 20 h. After cooling to room temperature, the mixture was added dropwise to ether (60 mL). The precipitate (which slowly liquified) was filtered and dried at room temperature under vacuum.

$^1$H-NMR: 9.87 (br.), 8.79 (br.), 8.13 (br.), 7.92, 5.83, 5.14 (br.), 4.51 (br.), 4.12 (br.), 3.82, 3.55, 3.47, 3.39, 3.30, 3.25, 3.01 (br.), 2.87 (br.), 2.76 (br.), 2.70, 2.66, 2.56 (br.), 2.50, 2.17, 2.05, 1.91, 1.68, 1.28, 1.01.

b) Preparation of Random poly(succinimide-co-[N-(3,4-dihydroxyphenethyl)aspartamide]-co-[N-(2-[(4-oxo-4-{2,6,6-trimethylcyclohexa-1,3-dien-1-yl}butan-2-yl)thio]ethyl)aspartamide]) 20

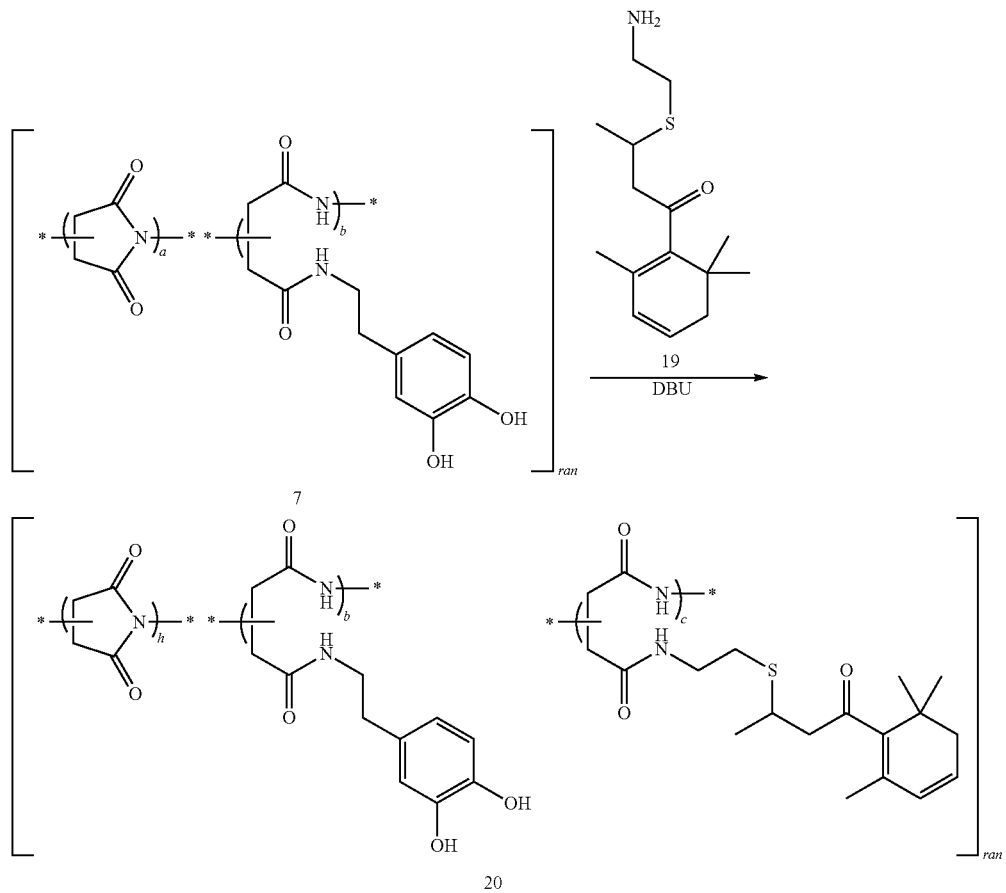

h = 72/100, b = 20/100, c = 8/100

In a 25 mL round-bottomed flask, co-polymer 7 (0.75 g, 5.1 mmol) was dissolved in NMP (7.5 mL) to give a brown solution. Then 19 (mixture prepared as described above, 0.60 g, 1.0 mmol) and DBU (120 mg, 0.79 mmol) were added. The reaction mixture was stirred at 80° C. for 20 h. After cooling to room temperature, the mixture was poured onto heptane (50 mL) and stirred for 30 min. The NMP phase was separated and acetone (1.2 mL) was added. The mixture was added dropwise to ethanol (50 mL) and concentrated, taken up in toluene and concentrated. Then acetone (5 mL) was added and the precipitate filtered, washed with acetone and dried at 50° C. under vacuum.

$^1$H-NMR: 9.67 (br.), 8.79 (br.), 7.99, 7.92, 7.25, 7.18, 6.59, 6.42, 5.86, 5.83, 5.05 (br.), 4.51 (br.), 4.17 (br.), 3.82, 3.54, 3.47, 3.38, 3.30, 3.24, 3.15 (br.), 3.02 (br.), 2.87 (br.), 2.76 (br.), 2.70, 2.65, 2.56, 2.51, 2.30, 2.18, 2.09, 2.04, 1.90, 1.67, 1.61, 1.54, 1.36, 1.27, 1.01.

Example 7

Dynamic Headspace Analysis of the Release of a Perfuming Ingredient from the Invention's Co-Polymers Incorporated into a Consumer Product (Fabric Softener)

The use as perfuming ingredient of the present invention's co-polymer has been tested in a fabric softening application using a fabric softener base with the following composition: Stepantex® VK90 (origin: Stepan) 16.5%, calcium chloride (10% in water) 0.6% and demineralized water 82.9%. The perfuming performance of the free odoriferous α,β-unsaturated ketone and of the invention's co-polymer was compared on dry fabric after 3 days using dynamic headspace analysis.

In a small vial, 1 mL of the co-polymer 8a prepared in Example 3 (69.9 mg at 25% in benzyl benzoate to improve the dispersion of the co-polymer in the softener formulation) in ethanol was added to 1.80 g of the above described fabric softener base and left standing for 15 h. Then the sample was placed in a beaker and diluted with ca. 600 g of demineralized cold tap water. One cotton sheet (EMPA cotton test cloth Nr. 221, origin: Eidgenossische Materialprufanstalt (EMPA), pre-washed with an unperfumed detergent powder and cut to ca. 12×12 cm sheets) was added and agitated manually for 3 min, left standing for 2 min, then wrung out by hand and weighed to ensure a constant quantity of residual water. As a reference sample, 1 mL of a solution containing an equimolar amount of unmodified trans-6-damascone (8.7 mg in 1 mL of ethanol) was added to another 1.80 g of the fabric softener base which was treated as described above. All cotton sheets were line-dried for 3 days.

To determine the headspace concentration of trans-δ-damascone, each of the dry cotton sheets was put into a headspace sampling cell (internal volume ca. 160 mL), thermostatted at 25° C. and exposed to a constant air flow of ca. 200 mL/min, respectively. The air was filtered through active charcoal and aspirated through a saturated solution of NaCl. During 15 min the volatiles were adsorbed onto a waste Tenax® cartridge, then during 15 min on a clean Tenax® cartridge. The sampling was repeated 7 times every 60 min (45 min trapping on the waste cartridge and 15 min on a clean cartridge). The cartridges were desorbed on a Perkin Elmer TurboMatrix ATD 350 desorber coupled to an Agilent 7890A gas chromatograph equipped with a HP-5 MS capillary column (30 m, i.d. 0.25 mm, film 0.25 μm) and a FID detector. The volatiles were analyzed using a two-step temperature gradient starting from 60° C. (for 1 min) to 200° C. at 15° C./min and then going to 260° C. at 25° C./min. To quantify the amount of trans-6-damascone in the headspace, external standard calibrations were carried out using four different concentrations of trans-6-damascone in ethanol. 2 μL of each calibration solution were injected onto three clean Tenax® cartridges, respectively. All the cartridges were desorbed immediately under the same conditions as those resulting from the headspace sampling.

The following amounts of trans-δ-damascone were detected from the sample containing the co-polymer 8a prepared in Example 3 as compared to the reference sample with unmodified trans-δ-damascone. All data are average values of two measurements:

| Headspace sampling time [min] | Amount of trans-δ-damascone (reference) after drying for 3 d [ng/L] | Amount of trans-δ-damascone released from the invention's co-polymer 8a prepared in Example 3 after drying for 3 d [ng/L] |
| --- | --- | --- |
| 30 | 0.8 | 7.0 |
| 90 | 0.6 | 12.2 |
| 150 | 0.5 | 15.4 |
| 210 | 0.5 | 16.7 |
| 270 | 0.5 | 17.3 |
| 330 | 0.5 | 17.9 |
| 390 | 0.5 | 18.6 |
| 450 | 0.5 | 21.8 |

The data show that the amount of trans-δ-damascone released from the invention's co-polymer over dry fabric was significantly higher as compared to the unmodified free fragrance molecule. After sampling for 450 min, an increase of the headspace concentration by a factor of about 40 was observed after 3 days, thus illustrating the desired increase of long-lastingness obtained by using the co-polymers according to the invention.

Example 8

Olfactive Evaluation of the Release of a Perfuming Ingredient from the Invention's Co-Polymers Incorporated into a Consumer Product (Liquid Detergent)

The tests were carried out using a standard liquid detergent base, generally used to treat terry towels.

The washing of the terry towels was carried out with 75 g of an un-perfumed detergent base to which were previously added pure trans-δ-damascone (0.05%) or, alternatively, the corresponding molar amount of trans-δ-damascone releasing co-polymer 8a prepared in Example 3.

As a further reference, we compared the performance of the invention's co-polymers of formula (I) to the free oil trans-δ-damascone, which was prepared and treated in the same way as described above.

A washing machine (Miele Novotronic W300-33CH) was loaded with 10 small terry towels (18 cm*18 cm, about 30 g each) and 6 kg of large cotton towels. The load was washed at 40° C. using a short cycle program and rinsed twice at 900 rpm.

At the end of the washing, the 10 small terry towels were line-dried for 24 h and wrapped into aluminium foil for storage, before being evaluated in intensity and assessment by 20 panelists after 3 and 7 days, using a scale ranging from "1" (no odor) to "7" (very strong).

The following average intensity and freshness (between brackets) for the different samples were determined:

| Tested molecule | Evaluation after 3 days | Evaluation after 7 days |
| --- | --- | --- |
| trans-δ-damascone (reference) | 2.3 | 1.8 |
| Co-polymer 8a | 2.9 | 2.2 |

The evaluation showed significant differences in intensity for the comparison of the two samples (0.5 unit of difference provide >99.9% of statistical significance). The towels containing the co-polymer described in Example 3 according to the invention was found to be stronger and fresher than the free oil.

Example 9

Comparison of the Release of Perfuming Ingredients from Different of the Invention's Co-Polymers Incorporated into a Consumer Product (Fabric Softener)

The use as perfuming ingredient of the present invention's co-polymers has been tested in a fabric softening application using a fabric softener base with the composition described in Example 7. The perfuming performance of free odoriferous α,β-unsaturated ketones and different of the invention's co-polymers was compared on dry fabric after 1 day using dynamic headspace analysis.

In a small vial, the co-polymers of the present invention were added to 1.80 g of the above described fabric softener base to release a total possible amount of 0.045 mmol of α,β-unsaturated ketone. Ethanol (0.5 mL) was added and the samples sonicated for several hours and stirred at room temperature overnight. As reference samples, 0.25 mL of a solution containing an equimolar amount of unmodified free odoriferous α,β-unsaturated ketone (0.045 mmol) was added to another 1.80 g of the fabric softener base and left stirring overnight. The samples were each placed in a beaker and diluted with ca. 600 g of demineralized cold tap water. Two cotton sheets (as described in Example 7) were added and agitated manually for 3 min, left standing for 2 min, then wrung out by hand, weighed to ensure a constant quantity of residual water and line-dried for 1 day. Each of the dry cotton sheets was put into a headspace sampling cell (internal volume ca. 160 mL), and the odoriferous α,β-unsaturated ketones released from the cotton surface were analyzed as outlined in Example 7. Tenax® cartridges were desorbed on a Perkin Elmer TurboMatrix ATD desorber coupled to an Agilent 7890A gas chromatograph equipped with a HP-1 capillary column (30 m, i.d. 0.32 mm, film 0.25 μm) and a FID detector. The volatiles were analyzed using a temperature gradient starting from 100° C. to 260° C. at 15° C./min. The amount of odoriferous α,β-unsaturated ketones in the headspace was determined by external standard calibration.

The following amounts of odoriferous α,β-unsaturated ketones were detected from the sample containing the co-polymers 8b and 13 (prepared in Example 3 and releasing trans-δ-damascone) and co-polymers 18 and 20 (prepared in Example 6 and releasing damascenone) as compared to the corresponding reference sample with unmodified trans-δ-damascone or damascenone. All data are average values of two measurements:

| Headspace sampling time | Amount of trans-δ-damascone (reference) after drying for 1 d | Amount of trans-δ-damascone released from the invention's co-polymers prepared in Example 3 after drying for 1 d [ng/L] | |
|---|---|---|---|
| [min] | [ng/L] | co-polymer 8b | co-polymer 13 |
| 30 | 1.3 | 23.1 | 18.3 |
| 90 | 1.5 | 57.0 | 39.9 |
| 150 | 1.8 | 68.0 | 48.9 |
| 210 | 1.2 | 71.7 | 53.1 |
| 270 | 0.8 | 67.2 | 53.4 |
| 330 | 0.5 | 72.3 | 58.3 |
| 390 | 0.8 | 74.6 | 58.3 |
| 450 | 0.8 | 75.6 | 59.6 |

| Headspace sampling time | Amount of damascenone (reference) after drying for 1 d | Amount of damascenone released from the invention's co-polymers prepared in Example 6 after drying for 1 d [ng/L] | |
|---|---|---|---|
| [min] | [ng/L] | co-polymer 18 | co-polymer 20 |
| 30 | 1.5 | 39.7 | 32.5 |
| 90 | 1.1 | 67.5 | 58.2 |
| 150 | 1.0 | 83.7 | 72.7 |
| 210 | 0.9 | 89.4 | 72.1 |
| 270 | 0.8 | 89.7 | 71.5 |
| 330 | 1.0 | 92.9 | 71.5 |
| 390 | 0.9 | 97.5 | 74.6 |
| 450 | 0.8 | 99.3 | 74.1 |

The data show that the amount of trans-δ-damascone or damascenone released from the invention's co-polymer over dry fabric was significantly higher as compared to the unmodified free fragrance molecule. After drying for 1 day and sampling for 450 min, an increase of the headspace concentrations by a factor varying between about 75 and 125 was observed, thus illustrating the desired increase of long-lastingness obtained by using the co-polymers according to the invention.

The invention claimed is:

1. A co-polymer derived from poly(aspartic acid), capable of releasing in a controlled manner an odoriferous α,β-unsaturated ketone or aldehyde, and comprising at least one repeating unit of formula (I-α) and/or (I-β)

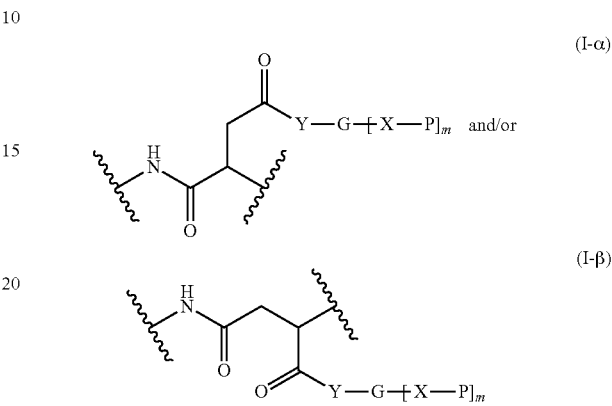

in the form of any one of their enantiomers or mixtures thereof, and wherein m is 1 or 2, and wherein the wavy lines (as for all the description) represent the bonding to another repeating unit, and P represents a radical susceptible of generating an odoriferous α,β-unsaturated ketone or aldehyde and is represented by formula

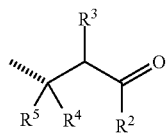
(II)

in which the hatched line indicates the location of the bond between said P and X;

$R^2$ represents a hydrogen atom, a $C_1$ to $C_{15}$ linear, cyclic or branched alkyl, alkenyl or alkadienyl radical, optionally substituted by one to four $C_1$ to $C_4$ alkyl groups; and $R^3$, $R^4$ and $R^5$ represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups;

or two, or three, of the groups $R^1$ to $R^4$ are bound together to form a saturated or unsaturated ring having 5 to 20 carbon atoms and, including the carbon atom to which said $R^2$, $R^3$, $R^4$ or $R^5$ groups are bound, this ring being possibly substituted by $C_1$ to $C_8$ linear, branched or cyclic alkyl or alkenyl groups; and with the proviso that at least one of the P groups is of the formula (II) as defined hereinabove;

X represents a functional group selected from the group consisting of the formulae i) to iii):

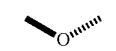
i)

ii)

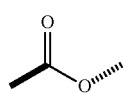
iii)

in which formulae the hatched lines are as defined above and the bold lines indicate the location of the bond between said X and G;

G represents a $C_2$-$C_8$ hydrocarbon group optionally comprising 1 or 2 oxygen, sulfur and/or nitrogen atoms;

Y represents an oxygen atom, a sulfur atom or a $NR^6$ group, $R^6$ representing a hydrogen atom or a $C_1$-$C_4$ alkyl group.

2. A co-polymer according to claim 1, characterized in that P represents a radical of the formulae (P-1) to (P-12), in the form of any one of its isomers:

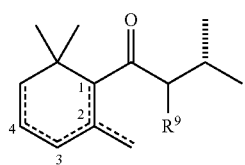
(P-1)

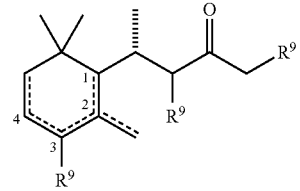
(P-2)

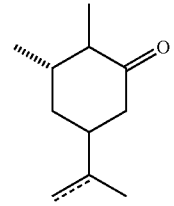
(P-3)

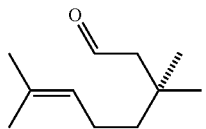
(P-4)

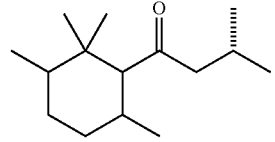
(P-5)

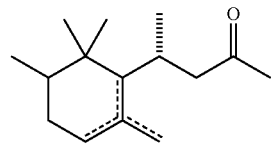
(P-6)

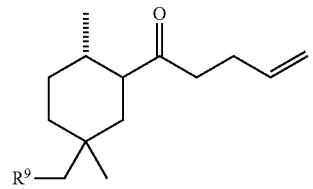
(P-7)

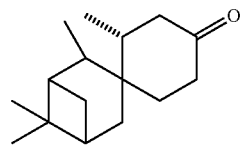
(P-8)

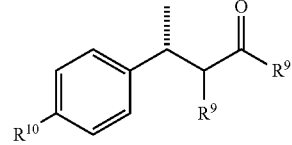
(P-9)

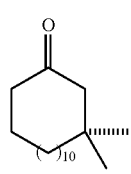
(P-10)

-continued

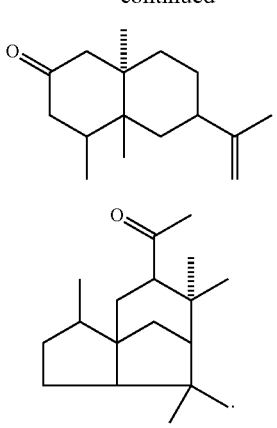

(P-11)

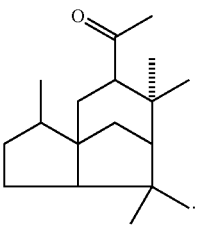

(P-12)

in which formulae the hatched lines have the meaning indicated above and the dotted lines represent a single or double bond, $R^9$ being a hydrogen atom or a methyl group and $R^{10}$ representing a hydrogen atom, a hydroxy or methoxy group or a $C_1$-$C_4$ linear or branched alkyl group.

3. A co-polymer according to claim 1, characterized in that said X represents a functional group of formula ii).

4. A co-polymer according to claim 1, characterized in that said Y represents an oxygen atom or a $NR^6$ group, $R^6$ representing a hydrogen atom or a methyl group.

5. A co-polymer according to claim 1, characterized in that m is 1.

6. A co-polymer according to claim 1, characterized in that said G represents a $C_2$-$C_5$ alkanediyl group optionally comprising one functional groups selected amongst ether, carboxylate or ester.

7. A co-polymer according to claim 1, characterized in that said co-polymer comprises at least one other repeating unit and said other repeating unit is of the formula (α) and/or (β) as well as of the formulae

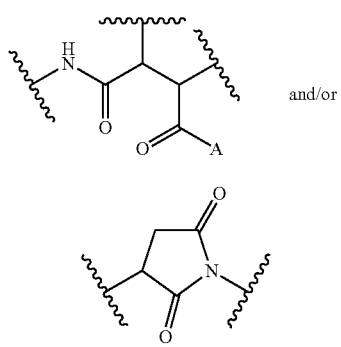

and/or (III)

(χ)

in the form of any one of their enantiomers or mixtures thereof, and wherein A represents:

i) a group of formula Y-G-[-X-M]$_m$, wherein m, Y, G and X are as defined in claim 1, and M represents a hydrogen or an alkali atom or a $C_{1-6}$ alkyl chain;

ii) a group of formula Y—$Z^1$, wherein Y is as defined in claim 1, and $Z^1$ represents a $C_{1-18}$ alkyl group;

iii) a group of formula Y—$Z^2$, wherein Y is as defined in claim 1, and $Z^2$ represents a poly(oxyalkylene) chain having from 10 to 50 oxyalkylene units consisting of ethylene glycol and/or propylene glycol repeating units; and/or iv) a group of formula Y—$Z^3$, wherein Y is as defined in claim 1, and $Z^3$ represents a —(CHQ)$_n$-CH$_2$-(ortho-C$_6$H$_3$(OH)$_2$) group where n is 0 or 1, Q is a hydrogen atom or a COOM group;

v) a group of formula Y—$Z^4$, wherein Y is as defined in claim 1, and $Z^3$ represents a —(CH$_2$)$_n$—(CH$_2$)$_2$—$R^7$ group where n is 0 or 1 and $R^7$ is hydroxyl group or $N(R^8)_2$ or $N(R^8)_3Q$ groups where $R^8$ is an hydrogen atom or a $C_1$-$C_{18}$ alkyl group and Q is chloride, bromide, methylsulfonate or methyl sulfate group.

8. A co-polymer according to claim 1, characterized in that said co-polymer comprises a ratio $(I)_{tot}/(Tot)$ comprised between 5/100 and 100/100, wherein $(I)_{tot}$ represents the amount of repeating units of formula (I-α) and/or (I-β), and (Tot) represents the amount of all repeating units present in the co-polymers.

9. A co-polymer according to claim 8, characterized in that said co-polymer comprises a ratio $(I)_{tot}/(Tot)$ comprised between 5/100 and 40/100.

10. A method for preparing a perfuming composition or perfumed product which comprises including the co-polymer of claim 1 as a perfuming ingredient in the composition or product.

11. A co-polymer according to claim 8, characterized in that said co-polymer comprises a ratio (I)tot/(Tot) comprised between 40/100 and 100/100.

12. A co-polymer according to claim 8, characterized in that said co-polymer comprises a ratio (I)tot/(Tot) comprised between 70/100 and 95/100.

13. A perfuming composition comprising:
i) as perfuming ingredient, at least one co-polymer as defined in claim 1;
ii) at least one ingredient selected from the group consisting of a perfumery carrier and a perfumery base; and
iii) optionally at least one perfumery adjuvant.

14. A perfuming consumer product comprising, as a perfuming ingredient, at least one co-polymer as defined in claim 1.

15. A perfuming consumer product according to claim 14, wherein the product is a perfume, a fabric care product, a body-care product, an air care product or a home care product.

16. A perfuming consumer product according to claim 14, wherein the product is a perfume, a hard surface cleaner, a fabric detergent or a softener base.

* * * * *